(12) United States Patent
Iftimia et al.

(10) Patent No.: US 9,655,521 B2
(45) Date of Patent: May 23, 2017

(54) COMBINED REFLECTANCE CONFOCAL MICROSCOPY-OPTICAL COHERENCE TOMOGRAPHY SYSTEM FOR IMAGING OF BIOLOGICAL TISSUE

(71) Applicant: Physical Sciences, Inc., Andover, MA (US)

(72) Inventors: Nicusor V. Iftimia, Chelmsford, MA (US); Mircea Mujat, Acton, MA (US); R. Daniel Ferguson, Melrose, MA (US); Ankit H. Patel, Methuen, MA (US); Milind Rajadhyaksha, New York, NY (US)

(73) Assignees: Physical Sciences, Inc., Andover, MA (US); Memorial Sloan-Kettering Cancer Center, New York, NY (US)

( * ) Notice: Subject to any disclaimer, the term of this patent is extended or adjusted under 35 U.S.C. 154(b) by 304 days.

(21) Appl. No.: 13/755,741

(22) Filed: Jan. 31, 2013

(65) Prior Publication Data

US 2014/0213897 A1   Jul. 31, 2014

(51) Int. Cl.
*A61B 5/05* (2006.01)
*A61B 5/00* (2006.01)

(52) U.S. Cl.
CPC .......... *A61B 5/0035* (2013.01); *A61B 5/0066* (2013.01); *A61B 5/0068* (2013.01)

(58) Field of Classification Search
None
See application file for complete search history.

(56) References Cited

U.S. PATENT DOCUMENTS

| | | | | |
|---|---|---|---|---|
| 2006/0227333 A1* | 10/2006 | Tearney et al. | | 356/512 |
| 2007/0046953 A1* | 3/2007 | De Groot et al. | | 356/512 |
| 2007/0081236 A1* | 4/2007 | Tearney et al. | | 359/390 |
| 2007/0177152 A1* | 8/2007 | Tearney et al. | | 356/477 |
| 2007/0229801 A1* | 10/2007 | Tearney et al. | | 356/73 |
| 2007/0252995 A1* | 11/2007 | Shaw | | 356/437 |
| 2008/0063998 A1* | 3/2008 | Liang | | A61B 1/0638 433/29 |

OTHER PUBLICATIONS

Altintas, M.A., et al., "Differentiation of superficial-partial vs. deep-partial thickness burn injuries in vivo by confocal-laser-scanning microscopy," ScienceDirect, Burns 35, 2009, pp. 80-86.
Chen, Alice C.-H., et al., "Second harmonic generation and multiphoton microscopic detection of collagen without the need for species specific antibodies," ScienceDirect, Burns 37, 2011, pp. 1001-1009.

(Continued)

*Primary Examiner* — Joseph M Santos Rodriguez
(74) *Attorney, Agent, or Firm* — Proskauer Rose LLP

(57) ABSTRACT

A dual-modality apparatus for imaging of biological tissue includes a reflectance confocal microscopy (RCM) imaging apparatus and an optical coherence tomography (OCT) imaging apparatus. A first optical component reflects a first beam of light provided by a RCM imaging apparatus towards a sample and passes a second beam of light provided by an OCT imaging apparatus towards the sample, such that the first and second beam of lights share at least a portion of an imaging path.

26 Claims, 18 Drawing Sheets

(56) References Cited

OTHER PUBLICATIONS

Iftimia, N., et al., "Combined RCM/OCT approach for real-time assessment of cancer lesions," Applications & Technology: Biomedical CLEO-2012 San Jose, CA, pp. 1-22.

Iftimia, N., et al., "Combined reflectance confocal microscopy/optical coherence tomography imaging for skin burn assessment," Biomedical Optics Express, vol. 4, No. 5, May 2013, pp. 680-695.

Jeng, J.C., et al., "Laser Doppler imaging determines need for excision and grafting in advance of clinical judgment: a prospective blinded trial," Elsevier Science Ltd., Burns 29, 2003, pp. 665-670.

Kaiser, M., et al., "Noninvasive assessment of burn wound severity using optical technology: A review of current and future modalities," ScienceDirect, Burns 37, 2011, pp. 377-386.

Kloppenberg, F.W.H., et al., "Perfusion of burn wounds assessed by Laser Doppler Imaging is related to burn depth and healing time," Elsevier Science Ltd., Burns 27, 2001, pp. 359-363.

Lange-Asschenfeldt, S., et al., "Applicability of confocal laser scanning microscopy for evaluation and monitoring of cutaneous wound healing," Journal of Biomedical Optics, downloaded from SPIE Digital Library on Aug. 5, 2012, pp. 1-10.

Pape. S.A., et al., "An audit of the use of laser Doppler imaging (LD1) in the assessment of burns of intermediate depth," Elsevier Science, Ltd., Burns 27, 2001, pp. 233-239.

Park, B. Hyle., et al.. "In vivo burn depth determination by high-speed fiber-based polarization sensitive optical coherence tomography," Journal of Biomedical Optics, vol. 6, No. 4, Oct. 2001, pp. 474-479.

Pierce, M.C., et al., "Collagen denaturation can be quantified in burned human skin using polarization-sensitive optical coherence tomography," Elsevier Ltd., Burns 30, 2004, pp. 511-517.

\* cited by examiner

COMBINED REFLECTANCE CONFOCAL MICROSCOPY-OPTICAL COHERENCE TOMOGRAPHY SYSTEM FOR IMAGING OF BIOLOGICAL TISSUE

GOVERNMENT RIGHTS

The invention was made with government support under U.S. Army Medical Research Department of Defense contract number W81XWH-11-C-0486 and National Cancer Institute NIH Grant No. R43CA162561. The government may have certain rights in the invention.

FIELD OF THE INVENTION

This invention relates generally to optical imaging, and more particularly, to apparatuses and methods for imaging of biological tissue with both Reflectance Confocal Microscopy imaging and Optical Coherence Tomography imaging.

BACKGROUND OF THE INVENTION

Imaging of biological tissue can aid in the diagnosis of skin cancers, oral cancers, and skin and/or oral burns. Reflectance Confocal Microscopy (RCM) is an imaging method that can show nuclear and cellular details of the biological tissue. For example, RCM can show details of the superficial epidermis of the biological tissue, the underlying papillae of the biological tissue, and the superficial reticular dermis of the biological tissue (e.g., to a depth of 250 µm). RCM can also show details of microcapillary blood flow in the upper dermis of the biological tissue. RCM imaging capabilities can include imaging the biological tissue at a depth that allows imaging of the dermo-epidermal junction (DEJ) of the biological tissue, e.g., a boundary between the superficial epidermis and the underlying deeper dermis of the biological tissue. RCM can enable noninvasive screening and diagnosis of cancers and/or burns while minimizing the need for biopsy.

RCM can produce grayscale en face images. Clinicians can find locating and delineating the DEJ based solely on RCM images to be challenging. Localization and delineation of the DEJ can be important in diagnosing skin and oral cancers. Melanomas and basal cell carcinomas can originate at the DEJ and can spread laterally from the DEJ in the epidermis and/or invade into the deeper dermis. The lateral spread and/or depth of invasion relative to the DEJ can be an important parameter for diagnosing the stage of cancer and/or determining whether to recommend a surgical or non-surgical treatment plan. RCM can have limited imaging depth. The limited imaging depth can be due to increasing aberrations and/or scattering at higher depths. Cancer and/or burn spreading depth can be difficult to assess using RCM alone.

Optical coherence tomography (OCT) is an imaging method that can provide cross-sectional images that show tissue morphology in depth and/or can be used to visualize the epidermal and dermal layers in human skin. Each layer can have different birefringence properties and appear differentiated in a polarization sensitive OCT (PS-OCT) image. OCT can allow visualization of tissue morphology in both the dermis and epidermis (e.g. to depths of about 1.5-2.0 mm). OCT can allow visualization of the DEJ. PS-OCT images can aid in evaluating collagen integrity in the dermis and tissue morphology. OCT images can aid in determining cancer depth spreading and/or burn injury depth. OCT typically does not provide adequate resolution to resolve sub-cellular details and diagnose early stage cancers.

Although other technologies for characterizing skin lesions, especially burns, have been previously tested (e.g. laser Doppler imaging, terahertz imaging, multispectral imaging, or even RCM and OCT independently), none of these technologies typically provides a substantially complete picture of tissue morphology and functionality. It is desirable for an imaging system to provide reliable and/or real-time data about tissue integrity. It is also desirable for an imaging system to provide viability status of biological tissue. It is also desirable for an imaging system to enable clinicians to efficiently and/or reliably assess epithelial lesions. It is also desirable for an imaging system to enable clinicians to efficiently and/or reliably monitor therapy outcomes.

SUMMARY OF THE INVENTION

One advantage of the invention is assessing tissue viability reliably. Another advantage of the invention is enhanced diagnosis of skin and/or oral tissue conditions. Another advantage of the invention is achieving real-time, noninvasive, and/or three-dimensional quantitative assessment of biological tissue. Another advantage of the invention is improved assessment of important parameters of biological tissue (e.g., microstructure, blood perfusion, and birefringence properties) typically needed to provide a reliable diagnosis. Another advantage of the invention is using a single imaging probe for both RCM and OCT modalities. Another advantage of the invention is co-registering the RCM and OCT images and/or displaying them substantially simultaneously and/or in real-time. Another advantage of the invention is providing comprehensive and/or complementary data sets using noninvasive techniques (e.g. RCM can show morphological details in the epidermis and upper dermis, while OCT can show structural features and/or delineate the DEJ).

Another advantage of the invention is an imaging objective design that images at two different wavelengths (e.g. at 830 nm and 1310 nm). Another advantage of the invention is an imaging probe that combines at least a portion of optical paths of the RCM and OCT beams. Another advantage of the invention is full utilization of the numerical aperture (NA) of the imaging objective in the RCM mode. Another advantage of the invention is underutilization of the NA in the OCT mode. Another advantage of the invention is detecting the DEJ and obtaining both structural data (e.g. tissue morphology data) and functional data (e.g. showing birefringence and presence of blood flow and/or perfusion).

In one aspect, the invention includes a dual-modality apparatus for high resolution imaging of biological tissue. The apparatus includes a reflectance confocal microscopy (RCM) imaging apparatus including a RCM source. The apparatus also includes an optical coherence tomography (OCT) imaging apparatus including an OCT source. The apparatus also includes a first optical component. The first optical component reflects, using a first surface of the first optical component, a first beam of light provided by the RCM source toward a sample. The first optical component also passes a second beam of light provided by the OCT source through a second surface of the first optical component toward a sample, such that the first beam of light and second beam of light share at least a portion of an imaging path. The first optical component also reflects, using the first surface of the first optical component, a first light returning from the sample and directs the first light returning from the sample to the RCM unit for imaging. The first optical component also passes, through the first surface of the first optical component, a second light returning from the sample to the OCT unit for imaging.

In some embodiments, the apparatus includes a second optical component that reflects the first beam of light toward the first optical component and reflects the first returning light toward the RCM unit. In some embodiments, the apparatus includes a third optical component that focuses the first beam of light and the second beam of light on an imaging sample. In some embodiments, the first optical component is a dichroic mirror. In some embodiments, the second optical component is a mirror. In some embodiments, the third optical component is an imaging objective.

In some embodiments, the imaging objective has a numerical aperture of about 0.8 to 1.0. In some embodiments, the imaging objective further comprises a broadband coating to cover the light spectrum between 800 nm and 1400 nm. In some embodiments, the first beam of light fully utilizes the numerical aperture of the imaging objective. In some embodiments, the second beam of light underutilizes the numerical aperture of the imaging objective. In some embodiments, the first beam of light has a wavelength of about 830 nanometers. In some embodiments, the second beam of light has a wavelength of about 1310 nanometers. In some embodiments, the OCT imaging apparatus is a PS-OCT imaging apparatus.

In another aspect, the invention involves a method of imaging biological tissue. The method involves providing a first light signal generated by a reflectance confocal microscopy (RCM) source and a second light signal generated by an optical coherence tomography (OCT) source. The method also involves delivering, via a common optical path, the first light signal and the second light signal to a sample. The method also involves detecting a third light signal from the sample with a RCM imager and a fourth light signal from the sample with an OCT imager. The method also involves generating a RCM image based on the third light signal and an OCT image based on the fourth light signal.

In some embodiments, the method involves displaying the RCM image and the OCT image simultaneously. In some embodiments, the OCT imager is a polarization sensitive OCT (PS-OCT) imager.

In another aspect, the invention involves a method of imaging biological tissue. The method involves combining an optical path of a reflectance confocal microscopy (RCM) imager and an optical path of a polarization sensitive optical coherence tomography (OCT) imager using a system of optics. The method also involves detecting a first light signal from a sample with the RCM imager and a second light signal from the sample with the OCT imager. The method also involves generating a RCM image of the sample using the first light signal and an OCT image of the sample using the second light signal.

In some embodiments, the method involves displaying the images acquired from the RCM imager and the OCT imager simultaneously. In some embodiments, the image acquired from the RCM imager is a detailed cellular image. In some embodiments, the image acquired from the OCT imager shows dermal and epidermal layers of human skin in the reflectance mode and a dermal-epidermal junction region in the polarization sensitive mode. In some embodiments, the method also involves diagnosing at least one skin or oral tissue condition.

In another aspect, the invention involves a method of imaging biological tissue. The method involves delivering to a sample, via a common optical path, a reflectance confocal microscopy (RCM) light beam and an optical coherence tomography (OCT) light beam. The method also involves receiving, using a RCM detector, a first light signal from the sample, the detector providing an electrical signal responsive to the first light signal at each of a plurality of locations along the detector, the electrical signal indicative of a RCM image of the sample. The method also involves receiving, using an OCT interferometer, a second light signal from the sample, the OCT interferometer combining the second light signal returning from the sample with a reference signal and producing an interference signal indicative of an OCT image of the sample. The method also involves generating a RCM image of the sample based on the first electrical signal. The method also involves generating an OCT image of the sample based on the interference signal.

In some embodiments, the method involves displaying the RCM and OCT images. In some embodiments, the OCT image is based on two orthogonal polarization states of the interference signal.

BRIEF DESCRIPTION OF THE DRAWINGS

The advantages of the invention described above, together with further advantages, may be better understood by referring to the following description taken in conjunction with the accompanying drawings. The drawings are not necessarily to scale; emphasis instead is generally placed upon illustrating the principles of the invention.

DETAILED DESCRIPTION OF THE INVENTION

Generally, the invention includes an imaging apparatus and methods that can provide both Reflectance Confocal Microscopy (RCM) and Optical Coherence Tomography (OCT) images in real time and/or substantially synchronously. The imaging apparatus can provide the RCM and OCT images using a single probe. The single probe can include optical components that combine at least a portion of imaging paths of RCM and OCT modalities (e.g. modes). The imaging apparatus can operate in RCM and OCT modes substantially simultaneously, as described in further detail below.

Figure 1:
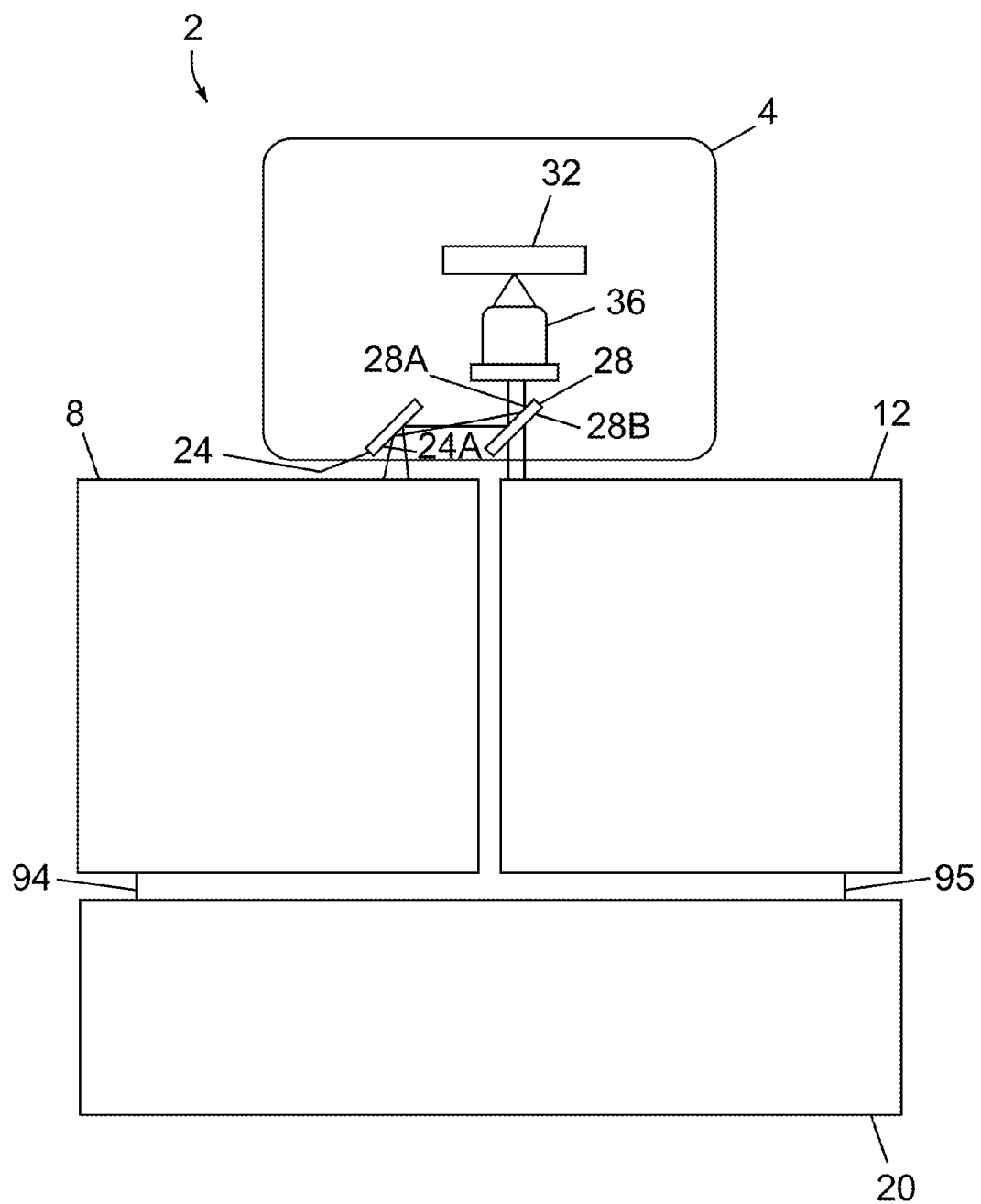
FIG. 1 is a diagram of an imaging apparatus, according to an illustrative embodiment of the invention.

FIG. 1 is a diagram of an imaging apparatus 2, according to an illustrative embodiment of the invention. The imaging apparatus 2 includes an imaging probe 4; a RCM imaging apparatus 8; an OCT imaging apparatus 12; and a control and data processing apparatus 20. The RCM imaging apparatus 8 and the OCT imaging apparatus 12 are each in communication with the imaging probe 4 and the system control and data processing apparatus 20.

The RCM imaging apparatus 8 provides a first beam of light for performing RCM imaging (e.g., in the RCM imaging modality) with the imaging apparatus 2. The first beam of light impinges on a first surface 24A of an optical element 24. The optical element 24 directs the first beam of light to a first surface 28A of an optical element 28. The optical element 28 directs the first beam of light to the optical element 36. The first beam of light passes through the optical element 36 toward a sample 32 (e.g., biological tissue) to be imaged. The RCM imaging apparatus 8 scans the first beam of light along the sample 32 via optical components 24, 28. The sample 32 reflects, absorbs, and/or backscatters the first beam of light. A portion of the reflected and/or backscattered light (e.g. a first returning light) returns to the RCM imaging apparatus 8. The first returning light travels through optical element 36 toward the first surface 28A of the optical element 28. The optical element 28 directs the first returning light to the first surface 24A of the optical element 24. The optical element 24 directs the first returning light to the RCM imaging apparatus 8. The RCM imaging apparatus 8 de-scans the first returning light and detects an image of the sample 32. The RCM imaging apparatus 8 outputs a first signal indicative of a RCM image via an electrical connection 94 to the system control and data processing unit 20 for data acquisition, processing, and/or display.

The OCT imaging apparatus 12 provides a second beam of light to the imaging probe 4. The second beam of light impinges on a second surface 28B of the optical element 28 and passes through the optical element 28 to the optical element 36. The second beam of light passes through the optical element 36 towards the sample 32. The second beam of light impinges upon the sample 32. The second beam of light can share a portion of an imaging path with the first beam of light. The sample 32 reflects, absorbs, and/or backscatters the second beam of light. A portion of the reflected and/or backscattered light (e.g. a second returning light) returns to the OCT imaging apparatus 12. The second returning light travels through the optical element 36 to the first surface 28A of the optical element 28. The second returning light passes through the optical element 28. The second returning light re-enters the OCT imaging apparatus 12. The OCT imaging apparatus 12 detects an image of the sample 32. The OCT imaging apparatus 12 outputs a second signal indicative of an OCT image via an electrical connection 95 to the system control and data processing unit 20 for data acquisition, processing and/or display.

In some embodiments, the optical element 24 is a mirror. In some embodiments, the optical element 28 is a dichroic mirror. In some embodiments, the optical element 36 is an imaging objective that adjusts the focus of light incident on it. In some embodiments, the optical element 36 is a system of lenses. In some embodiments, the RCM imaging apparatus 8 is a standard confocal microscope working in the reflection mode. In some embodiments, the OCT imaging apparatus 12 is a PS-OCT imaging apparatus. In some embodiments, the OCT imaging apparatus 12 is a standard spectrometer or swept-source based OCT instrument. It is apparent to one of ordinary skill in the art that the RCM imaging apparatus 8 and/or the OCT imaging apparatus 12 can be any apparatus capable of RCM imaging and OCT imaging, respectively, as is known in the art.

In some embodiments, the imaging probe 4 avoids using a dichroic mirror for reflection in the OCT mode, as dichroic mirrors can cause significant dispersion of light and degrade OCT image quality. In some embodiments, the optical element 36 further comprises a coating that allows beams of light along the light spectrum between approximately 800 nanometers and 1400 nanometers to pass. In some embodiments, the optical element 36 has a numerical aperture (NA) that is fully utilized in the RCM modality to permit high-resolution imaging. In some embodiments, the NA of the optical element 36 is underutilized in the OCT modality to permit imaging depths greater than about one millimeter. In some embodiments, the NA of the optical element 36 can be about 0.8-1.0.

Figure 2:
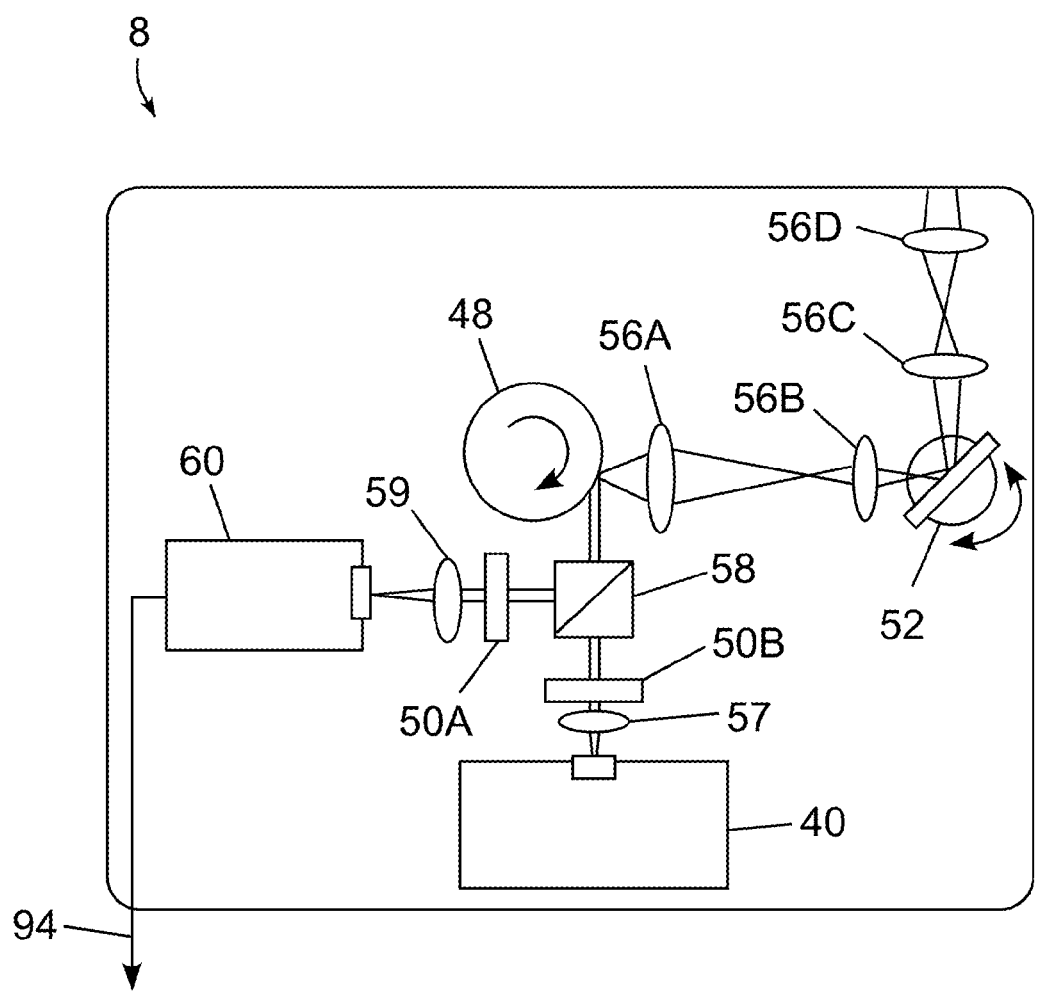
FIG. 2 is a diagram of a RCM imaging apparatus, according to an illustrative embodiment of the invention.

FIG. 2 is a diagram of a RCM imaging apparatus 8, according to an illustrative embodiment of the invention. The RCM imaging apparatus 8 includes a source 40 that provides a beam of light to an optical element 57 (e.g., a collimating lens). The optical element 57 collimates the beam of light and directs the beam of light to a polarizer 50B. The polarizer 50B directs the linear polarization component of the beam of light to a beam splitter 58. The beam splitter 58 splits the beam of light such that at least a portion of the beam is directed to the optical scanner 48. The optical scanner 48 scans the beam of light (e.g. generates a high speed line scan). The optical scanner 48 directs the beam of light to the optical scanner 52 through an optical path that includes lenses 56A, 56B, forming a telescope. The lenses 56A, 56B optically couple the optical scanner 48 with the optical scanner 52. The optical scanner 52 scans the beam of light into an orthogonal direction with respect to the linear scan (e.g. generates a low speed raster scan). The optical scanner 52 directs the beam of light toward the imaging probe (e.g. imaging probe 4 as shown above in FIG. 1) through an optical path that includes lenses 56C, 56D. The lenses 56C, 56D optically couple the optical scanner 52 with an optical element in the imaging probe (e.g. optical element 24 as shown above in FIG. 1).

Light returning from the imaging probe (e.g. a returning light) travels from the imaging probe to the RCM imaging apparatus 8. The returning light travels through the lenses 56D, 56C to the optical scanner 52. The optical scanner 52 de-scans the returning light. The optical scanner 52 directs the returning light through the lenses 56B, 56A to the optical scanner 48. The optical scanner 48 de-scans the returning light. The optical scanner 48 directs the returning light to the beam splitter 58. The beam splitter 58 directs at least a portion of the returning light to a polarizer 50A, which permits only a certain polarization of light to pass to a lens 59. The returning light travels through the lens 59 to impinge upon a detector 60. The detector 60 outputs a first electrical signal responsive to the returning light at a plurality of locations along the detector 60. The first electrical signal can be indicative of a RCM image of the sample. The first electrical signal travels through an electrical connection 94 to a system control and data processing apparatus (e.g. the system control and data processing apparatus 20 as shown above in FIG. 1).

In some embodiments, the source 40 is an 830 nanometer laser source. In some embodiments, the optical scanner 48 is a line scanner (e.g. a polygon scanner). In some embodiments, the optical scanner 52 is a low-speed raster scanner (e.g. a galvanometer manufactured by Cambridge Technology). In some embodiments, the detector 60 is an avalanche photodetector.

Figure 3:
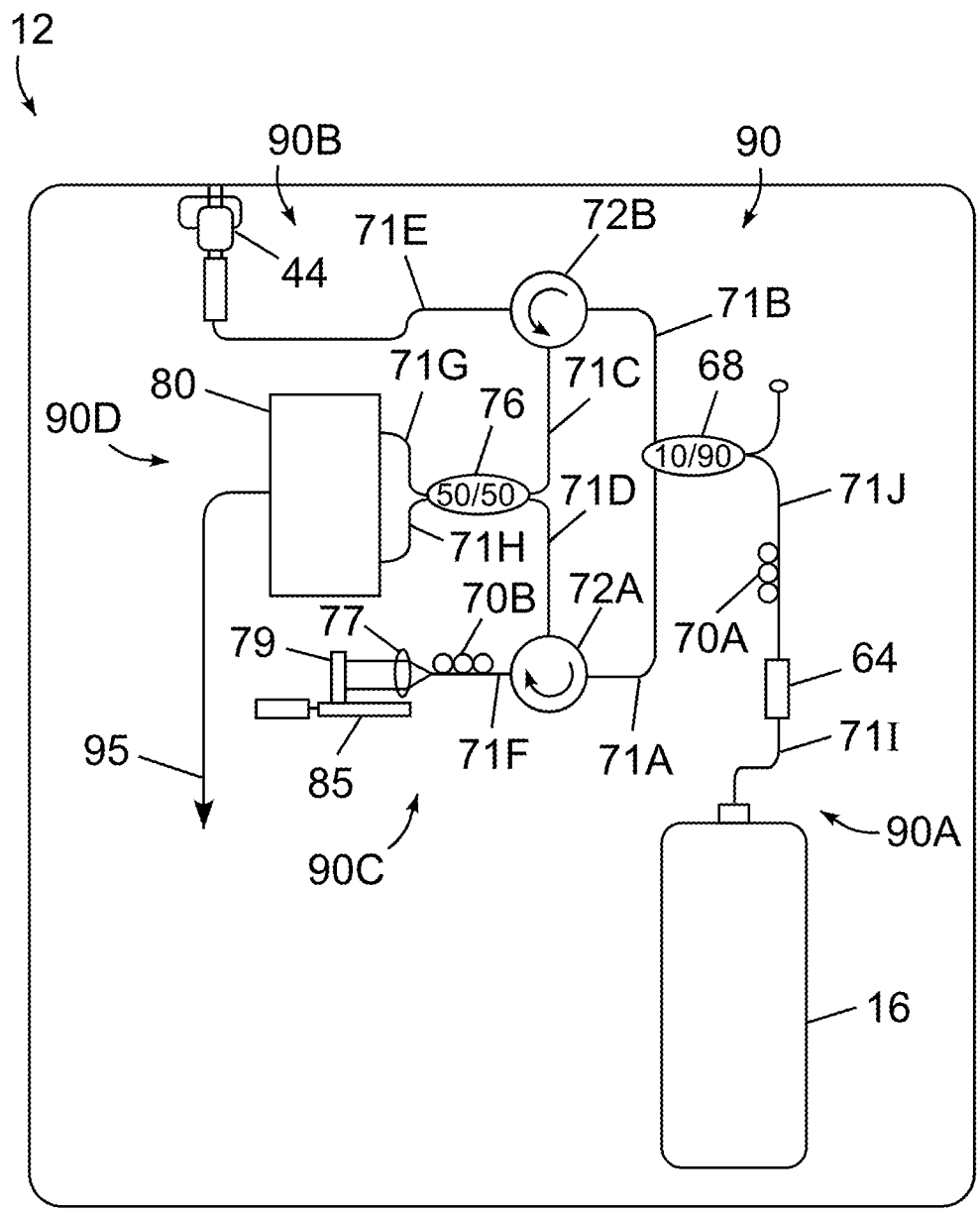
FIG. 3 is a diagram of an OCT imaging apparatus, according to an illustrative embodiment of the invention.

FIG. 3 is a diagram of an OCT imaging apparatus 12, according to an illustrative embodiment of the invention. The OCT imaging apparatus 12 includes a source 16, a dual spectrometer 80, a fiber optic interferometer 90, and OCT scanners 44.

The fiber optic interferometer 90 receives and/or directs light to four arms within the fiber optic interferometer 90: the illumination arm 90A, the sample aim 90B, the reference arm 90C, and the detection arm 90D. The fiber optic interferometer 90 includes a 10/90 splitter 68; two circulators 72A, 72B; a 50/50 polarization sensitive fiber combiner 76; polarization controllers 70A, 70B; a lens 77; a mirror 79; a translation stage 85; a phase modulator 64; and waveguides 71A, 71B, 71C, 71D, 71E, 71F, 71G, 71H, 71I, and 71J, generally 71.

During operation, the source 16 directs a beam of light to the phase modulator 64 via the waveguide 71I. The phase modulator 64 modulates the phase of the beam of light and directs the beam of light to the polarization controller 70A. The polarization controller 70A adjusts the polarization of the beam of light and directs the beam of light to the 10/90 splitter 68 via the waveguide 71J. The 10/90 splitter 68 divides the beam of light and directs a portion of the beam of light to the sample arm 90B and a portion of the beam of light to the reference arm 90C. Light entering the sample arm 90B travels via the waveguide 71B through the circulator 72B. The light is directed from the circulator 72B to the OCT scanners 44 via the waveguide 71E. The OCT scanners 44 direct the light to the imaging probe (e.g. imaging probe 4 as shown above in FIG. 1). Light returning from the imaging probe (e.g. returning light) is directed back to the circulator 72B via the waveguide 71E. The circulator 72B directs the returning light to the 50/50 polarization sensitive fiber combiner 76 via the waveguide 71C.

Light entering the reference arm 90C travels via the waveguide 71A to the circulator 72A. The circulator 72A directs the light to the polarization controller 70B via the waveguide 71F. The polarization controller 70B polarizes the light and directs the light to impinge on the lens 77. The light passes through the lens 77 to the mirror 79. The mirror 79 is positioned atop the translation stage 85. The translation stage 85 allows the position of the mirror to be adjusted so that the length of the reference arm 90C matches the length of the sample arm 90B.

A portion of the light directed to the reference arm 90C is reflected by the mirror 79. The reflected light passes through the lens 77 to the polarization controller 70B. The polarization controller 70B adjusts the polarization of the light to match the polarization of the light from the sample arm 90B, such that, for example, polarization changes caused by bending and rotation of the optical fiber in both the sample arm 90B and the reference arm 90C do not wash out the interference fringes. The light travels via the waveguide 71F to the circulator 72A. The circulator 72A directs the light to the 50/50 polarization sensitive fiber combiner 76 via the waveguide 71D.

Light entering the detection arm 70D travels to the 50/50 polarization sensitive fiber combiner 76 via the waveguides 71C, 71D. The light travels to dual spectrometer 80 via the waveguides 71G, 71H. Each spectrometer of dual spectrometer 80 receives an orthogonal polarization state of the light coming from the sample, such that change in the polarization status of the light induced by the sample can be monitored. The dual spectrometer 80 provides a signal indicative of an OCT image of the sample. The signal travels via an electrical connection 95 to a system control and data processing apparatus (e.g. the system control and data processing apparatus 20 as shown above in FIG. 1).

The dual spectrometer 80 can include diffraction gratings, spectrometer lens systems, and/or digital cameras. In some embodiments, the digital cameras can be InGaAs cameras. In some embodiments, the dual spectrometer 80 includes two InGaAs cameras. In some embodiments, the InGaAs cameras each have 1024 elements and/or a 25 millimeter active area. The InGaAs cameras can be used to collect two perpendicular polarization states of light coming from the 50/50 polarization sensitive fiber combiner 76. The dual spectrometer 80 can use specially designed diffraction gratings and lens systems to accommodate a spectral bandwidth of over 120 nanometers.

In some embodiments, the dual spectrometer 80 can be replaced with a balance detection scheme. In some embodiments, the source 16 can be replaced with a sweeping wavelength light source (e.g. a swept source approach). In some embodiments the sweeping wavelength light source can be a bulk optics polarization combiner. In some embodiments, all the fiber optic components can use polarization maintaining fibers. In some embodiments, the phase modulator 64 can be replaced with an in line fiber polarizer.

In some embodiments, the OCT imaging apparatus 12 is a PS-OCT imaging apparatus. In some embodiments, the OCT light source 16 is a broadband super-luminescent diode manufactured by DenseLight Semiconductors in Los Angeles, Calif. The OCT light source 16 can have a central wavelength of about 1310 nanometers and a bandwidth of about 135 nanometers. In some embodiments, the axial resolution of a broadband source (e.g. a broadband super-luminescent diode) can be determined as follows:

$$l_z = 0.44 \frac{\lambda_0^2}{n \Delta \lambda} \quad \text{EQN. 1}$$

where $\lambda_0$ is the center wavelength of the light source, $\Delta\lambda$ is the spectral width of the light source, and n is the refractive index of the sample. For biological tissues, n can be about 1.34. For air, n can be about 1.00. In some embodiments, the axial resolution $l_z$ provided by an OCT light source with $\lambda_0$ equal to 1310 nanometers and $\Delta\lambda$ equal to 135 nanometers is about 5.6 µm in air and about 4.2 µm in biological tissue.

Figure 4:
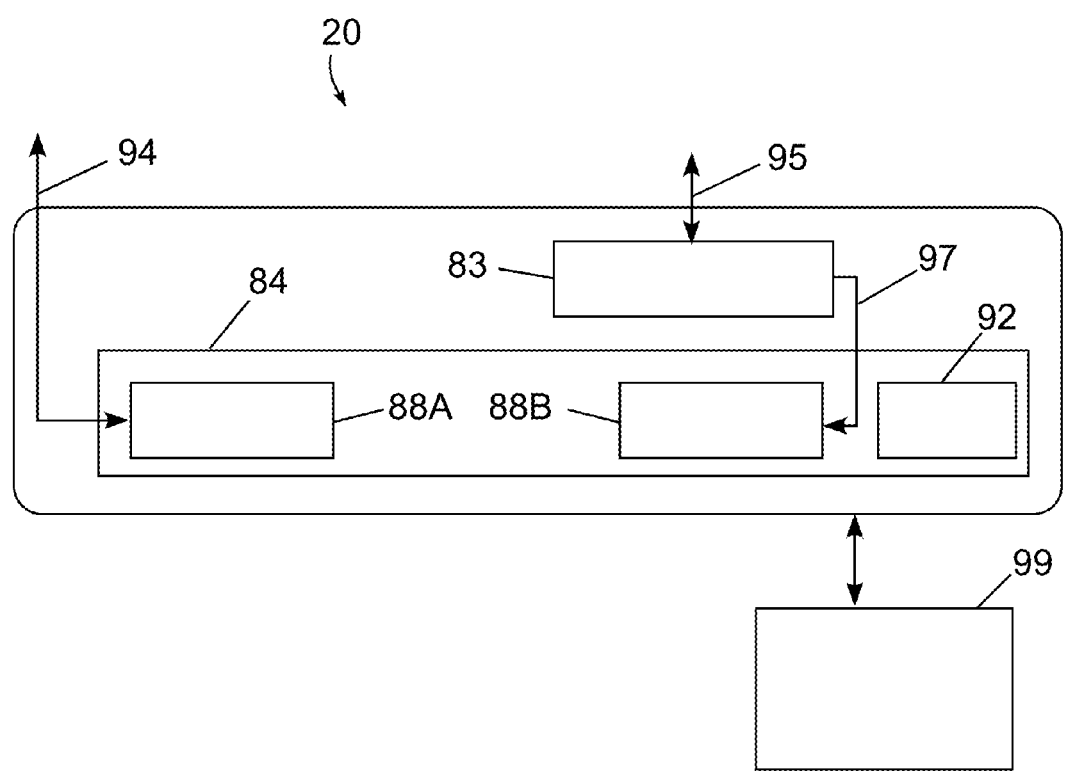
FIG. 4 is a diagram of a system control and data processing apparatus, according to an illustrative embodiment of the invention.

FIG. 4 is a diagram of a system control and data processing apparatus 20, according to an illustrative embodiment of the invention. The system control and data processing apparatus 20 includes a real-time digital signal processing (RT-DSP) board 83, a computer 84, and a display 99. The computer 84 includes frame grabbers 88A, 88B, and a data acquisition board 92.

The RT-DSP board 83 is in communication with the computer 84. The computer 84 includes frame grabbers 88A, 88B and a data acquisition board 92.

The RT-DSP board 83 receives and/or processes an imaging output (e.g., the second signal as described above in FIG. 1) from an OCT imaging apparatus (e.g., OCT imaging apparatus as described above in FIG. 3). In some embodiments, the RT-DSP board 83 can be programmed and/or adapted to control both the RCM and OCT scanners and/or process both the RCM and OCT signals. In some embodiments the RT-DSP board 83 communicates with the data acquisition board 92 via the PCI bus.

Frame grabber 88A is in communication with a RCM imaging apparatus (e.g. RCM imaging apparatus 8 as described above in FIG. 2). Frame grabber 88A receives imaging output from the RCM imaging apparatus via an electrical connection 94 such that the system control and data processing apparatus 20 can generate and/or display a RCM image. Frame grabber 88B is in communication with the RT-DSP board 83. The RT-DSP board 83 receives output from the OCT imaging apparatus via an electrical connection 95. The RT-DSP board 83 provides OCT imaging output to the frame grabber 88B via an electrical connection 97. Frame grabbers 88A, 88B each digitize their respective received outputs. The frame grabber 88A generates a RCM image of the sample 32. The frame grabber 88B generates an OCT image of the sample. Each of the images is provided to a display 99 connected to the computer 84.

In some embodiments, the computer 84 includes an i7 Quad-Core Processor manufactured by Intel, Inc. In some embodiments, the RT-DSP board 83 is based on field-programmable gated-array (FPGA) hardware and can allow for OCT data processing and display at high frame rates. In some embodiments, the RT-DSP board 83 is a custom design board by Physical Sciences, Inc. (PSI) of Andover, Mass. that is capable of performing of the steps for processing OCT data (e.g. Fast Fourier Transform, linear interpolation, and/or dispersion compensation).

In some embodiments, the RT-DSP board 83 operates as a standalone device that communicates with the computer 84 via a PCI bus (not shown). In some embodiments, the RT-DSP board 83 is replaced with a commercially available graphical processing unit (GPU). In some embodiments, OCT display rates of greater than 90 frames per second are possible at an image resolution of 512×1024 pixels. This imaging speed can be 2-3 times faster than that of commercially available OCT systems, many of which use high speed and/or costly computers.

Figure 5:
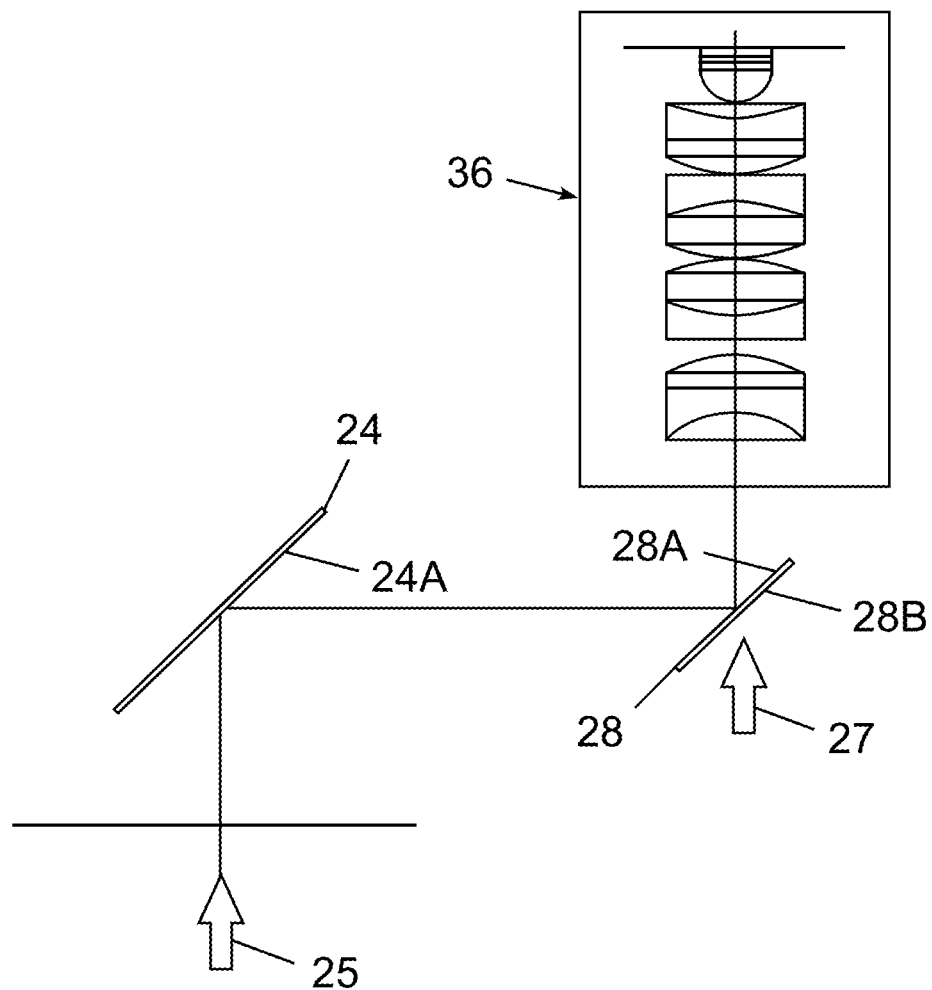
FIG. 5 is a diagram of a combined RCM/OCT optical path, according to an illustrative embodiment of the invention.

FIG. 5 is a diagram of a combined RCM/OCT optical path, according to an illustrative embodiment of the invention. The path includes optical elements 24, 28, and 36. In general, RCM light and OCT light each travel through optical element 36 to impinge on a sample to be imaged (e.g. the sample 32 as shown above in FIG. 1). Once impinged on the sample, the RCM light and OCT light are each reflected, absorbed, and/or backscattered back via the optical elements 36, 28, and/or 24 into their respective RCM and OCT imaging apparatuses.

RCM light is provided through a RCM insertion point 25. The RCM light impinges on a first surface 24A of an optical element 24. The optical element 24 directs the RCM light to a first surface 28A of an optical element 28. The optical element 28 directs the RCM light through an optical element 36 (e.g. a system of lenses and/or an imaging objective), which adjusts the focus of the incoming RCM light. The optical element 36 allows the RCM light to impinge on a sample (e.g. sample 32 as described above in connection with FIG. 1). A portion of the RCM light returns from the sample (e.g. a returning RCM light). The returning RCM light travels through the optical element 36 toward the first surface 28A of the optical element 28. The optical element 28 directs the returning RCM light to the first surface 24A of the optical element 24. The optical element 24 directs the returning RCM light to the RCM imaging apparatus (e.g. RCM imaging apparatus 8 as shown above in FIG. 2) for imaging.

OCT light is provided through an OCT insertion point 27. The OCT light impinges upon a second surface 28B of the optical element 28. The OCT light passes through the optical element 28 and is directed to the optical element 36. The OCT light impinges on the sample (e.g. sample 32 as shown above in FIG. 1). The OCT light can share a portion of an imaging path (e.g., including optical elements 28, 36) with the RCM light. A portion of the OCT light returns from (e.g. a returning OCT light). The returning OCT light travels through the optical element 36. The returning OCT light passes through the first surface 28A of the optical element 28. The returning OCT light re-enters the OCT imaging apparatus (e.g. OCT imaging apparatus 12 as shown in FIG. 3) for imaging.

Figure 6:
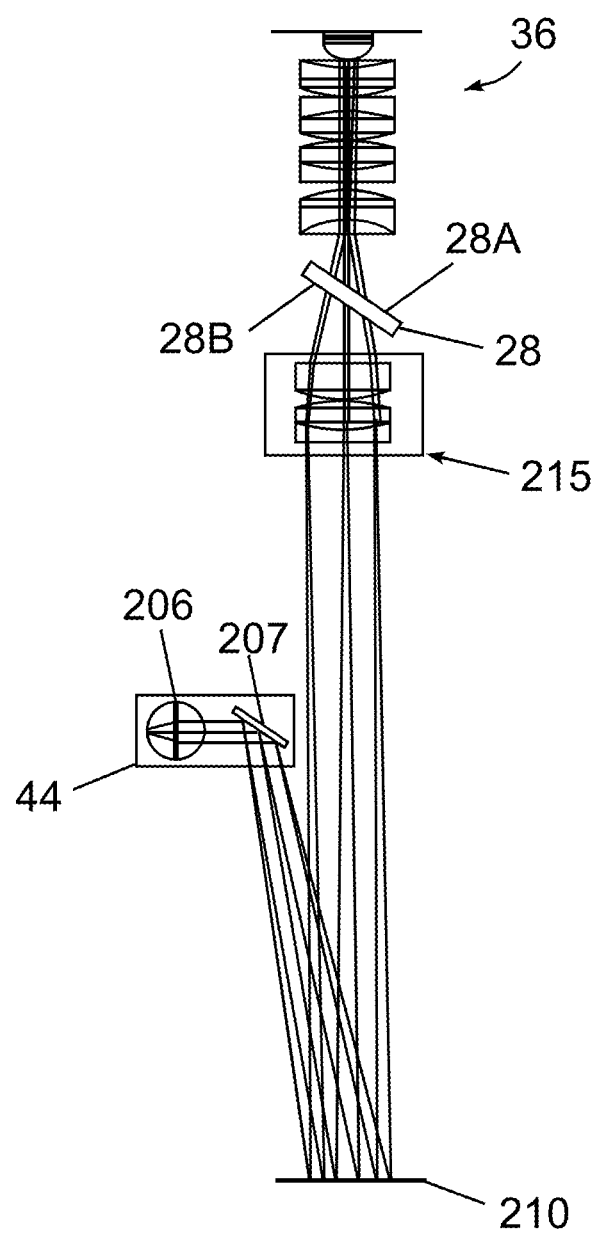
FIG. 6 is a diagram of an OCT imaging path, according to an illustrative embodiment of the invention.

FIG. 6 is a diagram of an OCT imaging path, according to an illustrative embodiment of the invention. The OCT imaging path includes OCT scanners 44 including a scan engine that includes mirrors 206, 207; a mirror 210; an optical element 28 including a first surface 28A and a second surface 28B; an optical element 36; and an optical element 215.

The OCT scanners 44 include a scan engine that includes mirrors 206, 207. During operation, an OCT beam is provided to the mirror 206. The mirror 206 directs the OCT beam to the mirror 207. The mirror 207 directs the OCT beam to the mirror 210. The mirror 210 directs the OCT beam to the optical element 215 (e.g. a set of relay lenses). The OCT beam impinges upon the second surface 28B of the optical element 28. The OCT beam passes through the optical element 28 and is directed to the optical element 36. The OCT beam travels through the optical element 36. The optical element 36 directs the OCT beam to a sample (not shown). The sample reflects, absorbs and/or backscatters the OCT beam. A portion of the reflected and/or backscattered light (e.g. a returning OCT light) passes through the optical element 36. The optical element 36 directs the returning OCT light to impinge upon the first surface 28A of the optical element 28. The returning OCT light passes through the optical element 28. The optical element 28 directs the returning OCT light to impinge on the optical element 215. The optical element 215 directs the returning OCT light to the optical element 210. The optical element 210 directs the returning OCT light to the mirror 207. The mirror 207 directs the returning OCT light to the mirror 206. The mirror 206 directs the returning OCT light to the OCT imaging apparatus (e.g. the sample arm 90B of the fiber optic interferometer 90 as shown above in FIG. 3).

In some embodiments, the mirrors 206, 207 are galvanometric mirrors. In some embodiments, the optical element 210 is a turning mirror. In some embodiments, the optical element 215 is a system of lenses. In some embodiments, the optical element 28 is a dichroic mirror. In some embodiments, the optical element 36 is an imaging objective and/or a system of lenses.

Figure 7:
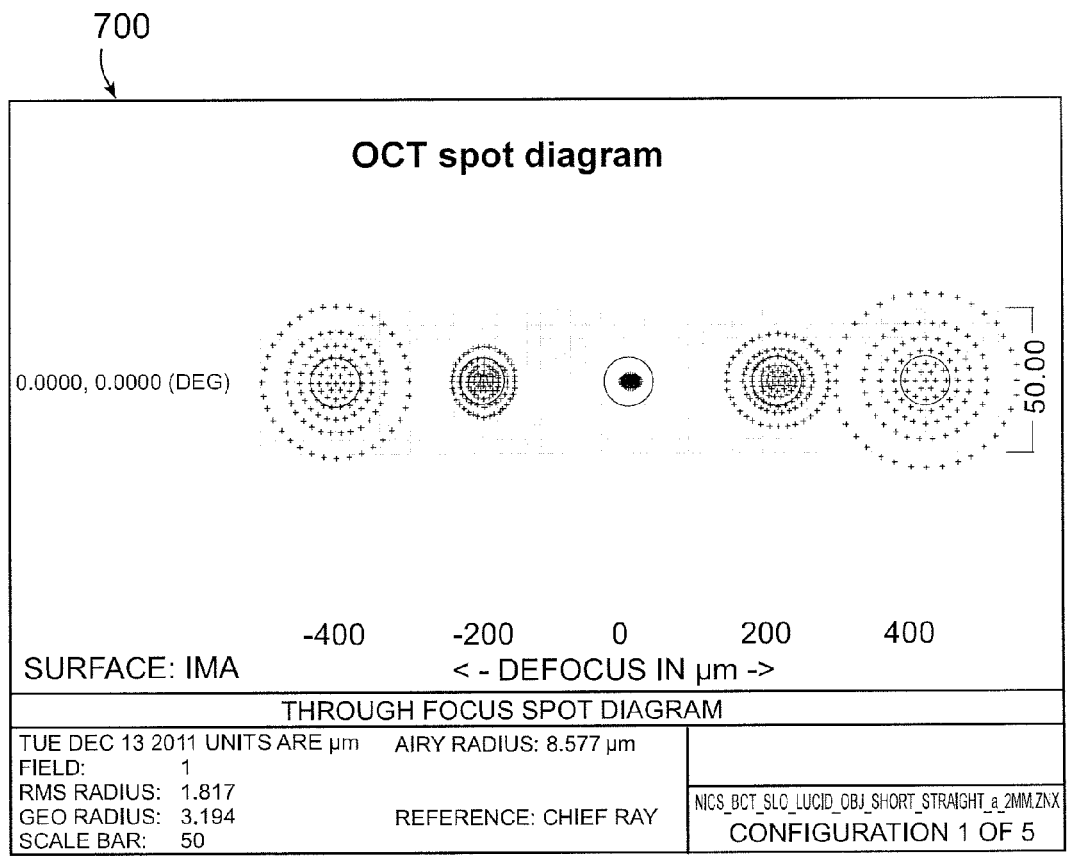
FIG. 7 is an OCT spot diagram, according to an illustrative embodiment of the invention.

FIG. 7 is an OCT spot diagram 700, according to an illustrative embodiment of the invention. Optical Zemax was performed to ensure optimum system performance of the OCT system. As observed, the energy of the OCT beam is focused within a less than 20 microns spot (e.g. an Airy disk) in the focal plane, and over a range of +/−0.4 mm most of the energy is still concentrated within the this diffraction limited spot. An imaging range of over 0.8 mm can be achieved in the OCT mode.

Figure 8:
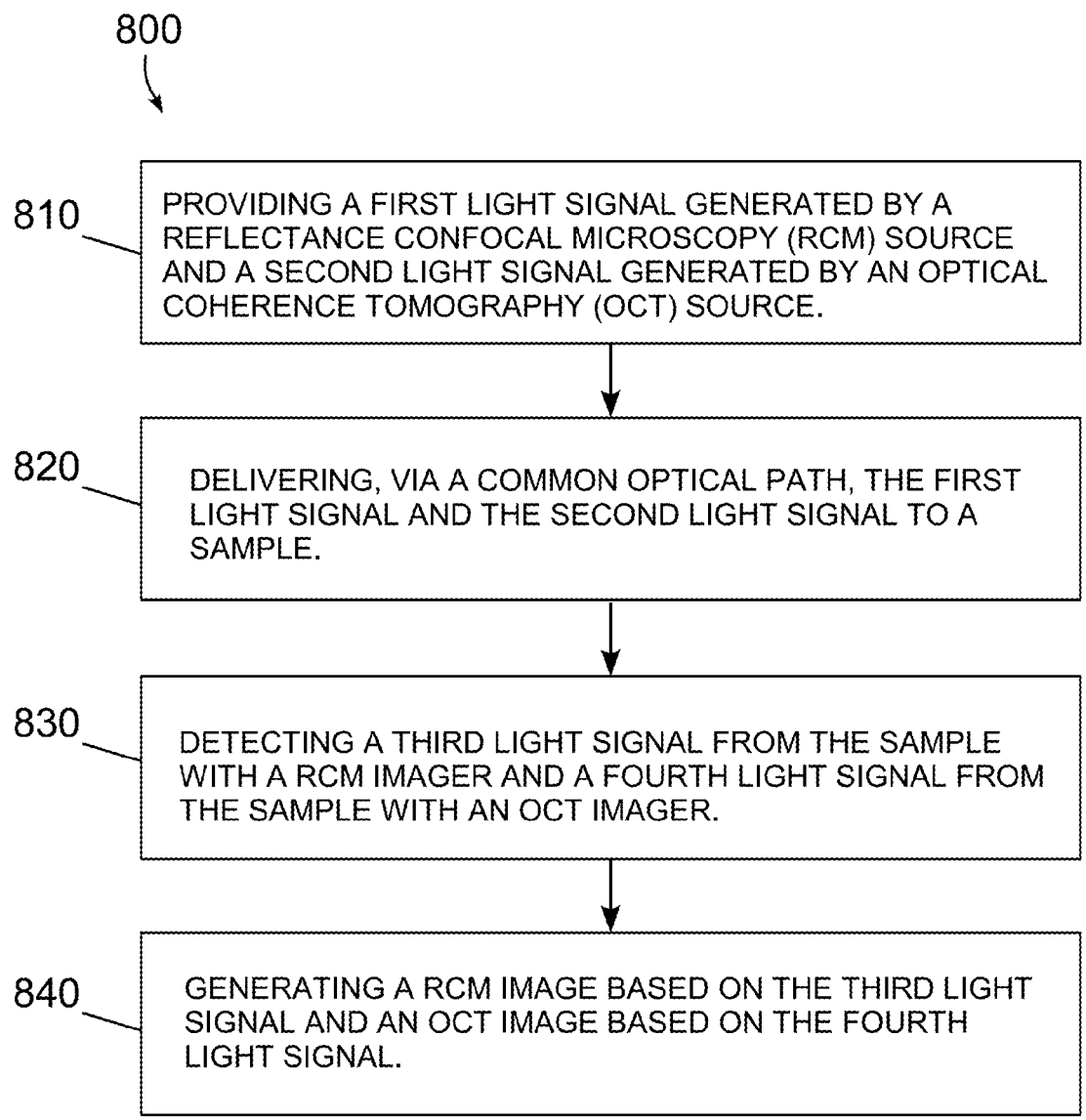
FIG. 8 is a flow chart illustrating a method of imaging biological tissue, according to an illustrative embodiment of the invention.

FIG. 8 is a flow chart illustrating a method 800 of imaging biological tissue, according to an illustrative embodiment of the invention. The method involves providing a first light signal generated by a RCM source (e.g., RCM source 40, as shown above in FIG. 2) and a second light signal generated by an OCT source (e.g., OCT source 16, as shown above in FIG. 3) (Step 810). The first light signal can have a power between approximately 2 and 20 mW. The first light signal can have a wavelength of 700 nm to 1000 nm. The second light signal can have a power between approximately 2 and 20 mW. The second light signal can have a wavelength of 1.3 to 1.5 microns.

The method 800 also involves delivering, via a common optical path, the first light signal and the second light signal to a sample (e.g., sample 32 as shown above in FIG. 1) (Step 820). The common optical path can include optical elements 28, 36 as shown above in FIG. 1.

The method 800 also involves detecting a third light signal coming from the sample with a RCM imager (e.g., RCM imaging apparatus 4, as shown above in FIG. 1) and a fourth light signal coming from the sample with a OCT imager (e.g., OCT imaging apparatus 12 as shown above in FIG. 1) (Step 830).

The method 800 also involves generating a RCM image (e.g. RCM image 1102 as shown below in FIGS. 11B-D) based on the third light signal and an OCT image (e.g. OCT image 1101 as shown above in FIG. 11A) based on the fourth light signal (Step 840).

Figure 9:
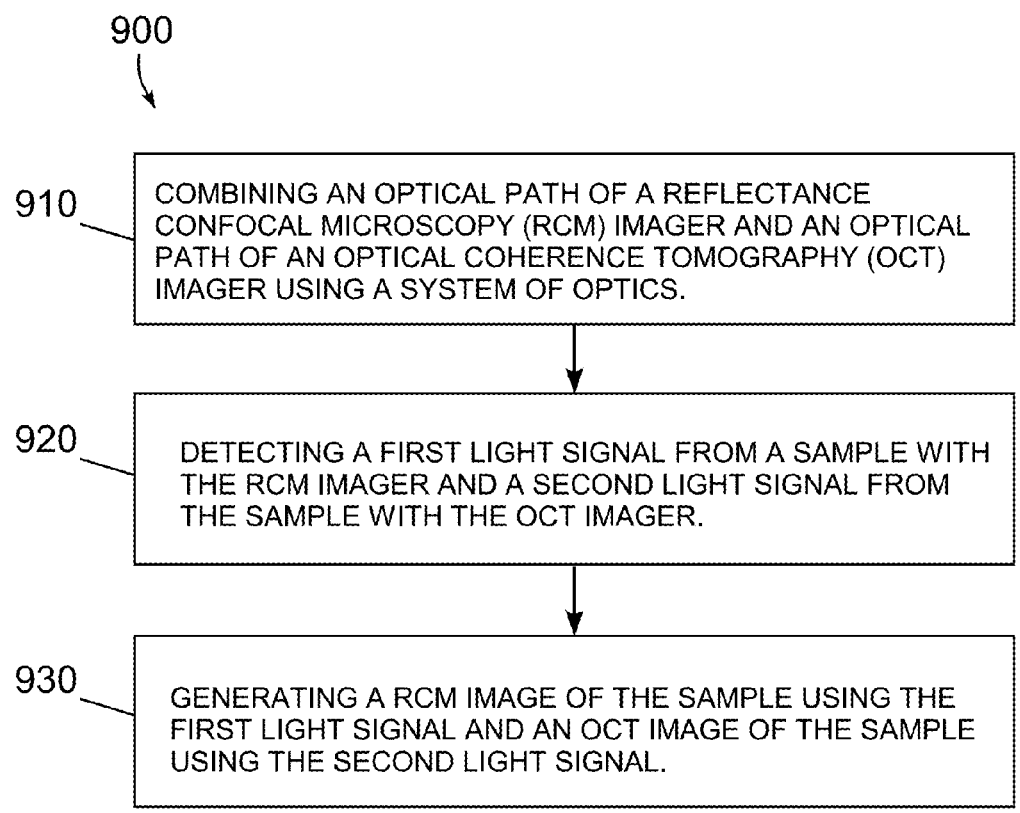
FIG. 9 is a flow chart illustrating a method of imaging biological tissue, according to an illustrative embodiment of the invention.

FIG. 9 is a flow chart illustrating a method 900 of imaging biological tissue, according to an illustrative embodiment of the invention. The method involves combining an optical path of a reflectance confocal microscopy (RCM) imager (e.g. RCM imaging apparatus 4 as shown above in FIG. 1) and an optical path of an optical coherence tomography (OCT) imager (e.g. OCT imaging apparatus 12 as shown above in FIG. 1) using a system of optics (Step 910).

The method 900 also involves detecting a first light signal from a sample with the RCM imager and detecting a second light signal from the sample with the OCT imager (Step 920).

The method 900 also involves generating a RCM image of the sample (e.g. RCM image 1102 as shown below in FIG. 11B) using the first light signal and OCT images (e.g. OCT image 1101 as shown below in FIG. 11A) using the second light signal (Step 930).

Figure 10:
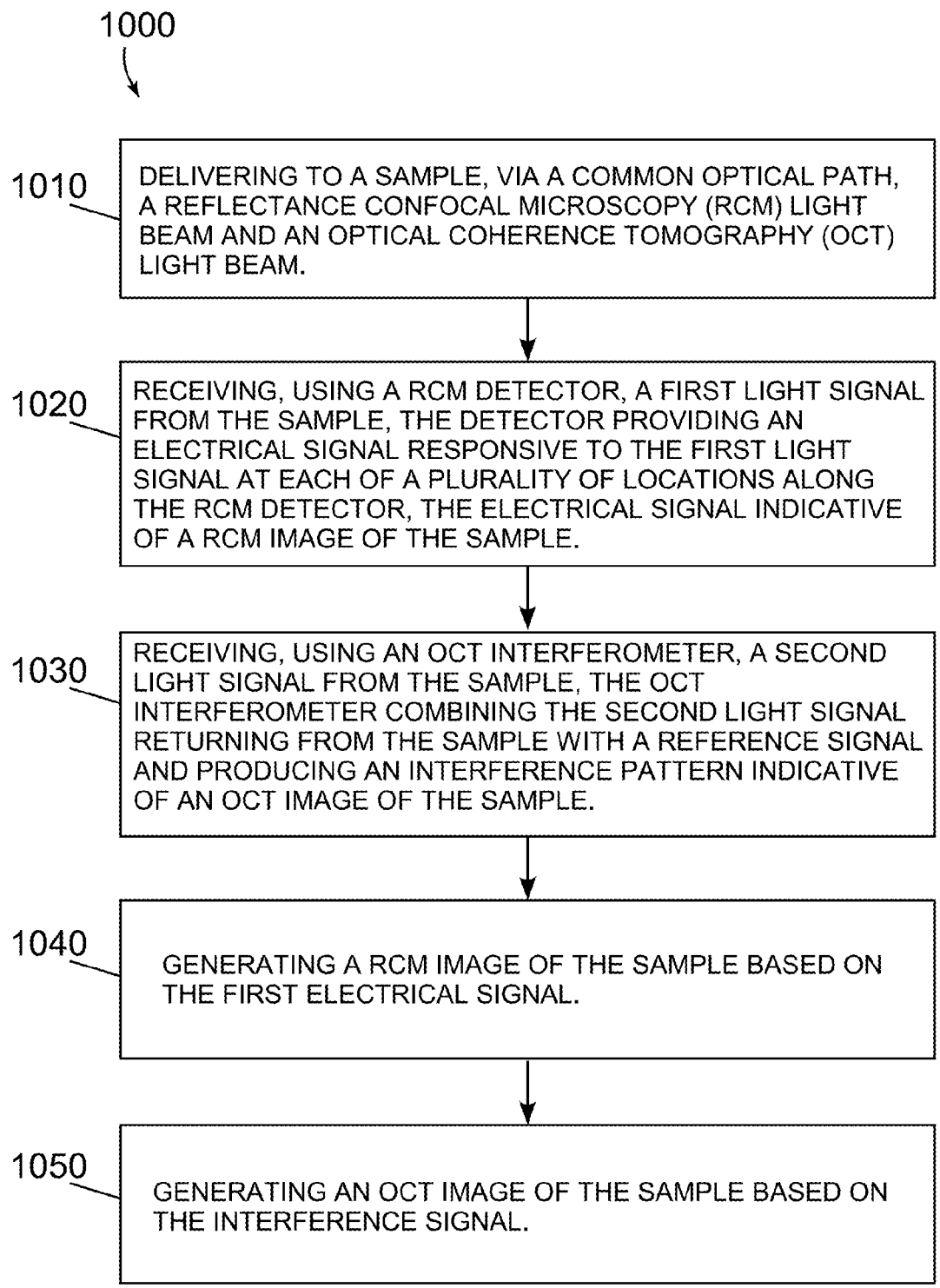
FIG. 10 is a flow chart illustrating a method of imaging biological tissue, according to an illustrative embodiment of the invention.

FIG. 10 is a flow chart illustrating a method 1000 of imaging biological tissue, according to an illustrative embodiment of the invention. The method 1000 involves delivering a reflectance confocal microscopy (RCM) light beam and an optical coherence tomogroaphy (OCT) light beam to a sample via a common optical path (Step 1010).

The method 1000 also involves receiving, using a RCM detector (e.g. RCM detector 60 as shown above in FIG. 2), a first light signal from the sample (e.g. sample 32 as shown above in FIG. 1), the RCM detector providing an electrical signal responsive to the first light signal at each of a plurality of locations along the RCM detector, the electrical signal indicative of a RCM image of the sample (Step 1020).

The method 1000 also involves receiving, using an OCT interferometer (e.g. interferometer 90 as shown above in FIG. 3), a second light signal from the sample, the OCT interferometer combining the second light signal returning from the sample with a reference signal and producing an interference signal indicative of an OCT image of the sample (Step 1030).

The method 1000 also involves generating a RCM image (e.g. RCM image 1102 as shown below in FIG. 11B) of the sample based on the first electrical signal (Step 1040).

The method 1000 also involves generating an OCT image (e.g. OCT image 1101 as shown below in FIG. 11A) of the sample based on the interference signal (Step 1050). The OCT image can be generated by a computer (e.g., computer 84 as shown above in FIG. 1).

FIGS. 11A-11D show exemplary RCM and OCT images of human skin of a ventral finger 1105 taken with an apparatus having an imaging probe (e.g., imaging probe 4, as shown above in FIG. 1), according to an illustrative embodiment of the invention.

Figure 11A:
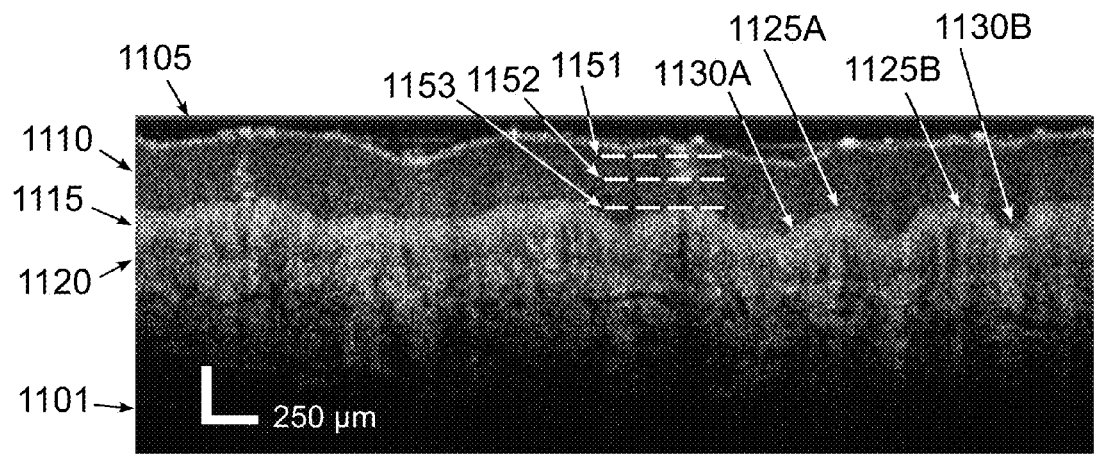
FIGS. 11A-11D show exemplary RCM and PS-OCT images of human skin of a ventral finger taken with an apparatus having an imaging probe, according to an illustrative embodiment of the invention
Figure 11B:
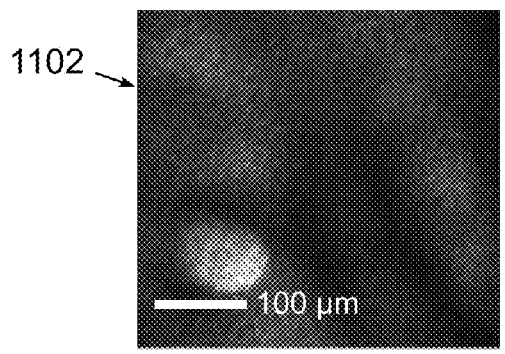
Figure 11C:
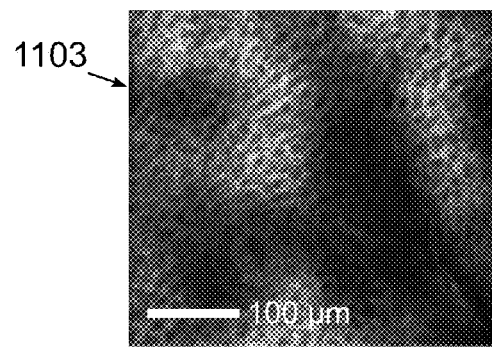
Figure 11D:
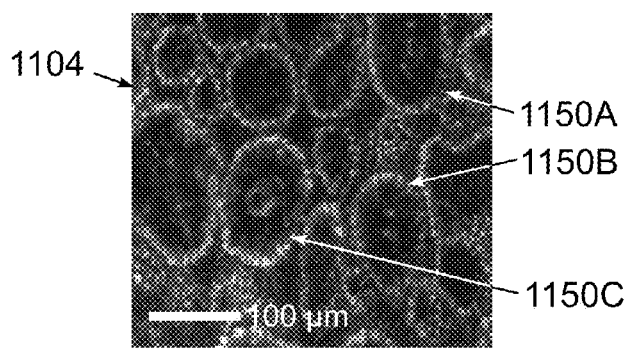

More specifically, FIG. 11A shows a cross-sectional OCT image 1101 of the ventral finger 1105. The cross-sectional OCT image 1101 shows an epidermal layer 1110 of the ventral finger 1105, an underlying dermis layer 1120 of the ventral finger 1105, and a dermo-epidermal junction 1115. The dermo-epidermal junction 1115 shows "hills and valleys" topography, including, e.g., hills 1125A, 1125B, generally 1125, and valleys 1130A, 1130B, generally 1130. The cross sectional OCT image 1101 shows depth levels of the ventral finger 1105, specifically, depth levels 1151, 1152, 1153. The depth level 1151 and the depth level 1152 are in the epidermal layer 1110. The depth level 1153 is in the underlying dermis layer 1120. FIGS. 11B-11D show RCM images that are orthogonal to the OCT image 1101 at depth levels, 1151, 1152, 1153, respectively. Each of the RCM images is shown with sub-micron resolution. The sweat glands observed in the OCT orthogonal plane can be recognized in the RCM image.

FIG. 11B shows a RCM image 1102 of the ventral finger 1105 that is orthogonal to the PS-OCT image 1101 at the depth level 1151 (as shown above in FIG. 11A). The RCM image 1102 shows 10 to 20 micron polygonal cells of the ventral finger 1105 with dark nuclei and bright, thin cytoplasm.

FIG. 11C shows a RCM image 1103 of the ventral finger 1105 that is orthogonal to the PS-OCT image 1101 at the depth level 1152 (as shown above in FIG. 11A). The RCM image 1103 shows 10 to 20 micron polygonal cells of the ventral finger 1105 with dark nuclei and bright, thin cytoplasm.

FIG. 11D shows a RCM image 1104 of the ventral finger 1105 that is orthogonal to the PS-OCT image 1101 at the depth level 1153. The RCM image 1104 shows basal cells of the ventral finger 1105, circumscribed by a rim of refractive cells, shown as rings 1150A, 1150B, 1150C, generally 1150. Viewing FIG. 11A together with any of FIGS. 11B-11D can provide a more complete understanding of the cellular details and tissue morphology of the ventral finger 1105 and can better enable the detection and staging of oral or skin lesions.

FIGS. 12A-12E show exemplary RCM and PS-OCT images of a resolution target 1210 and human skin taken with an apparatus having an imaging probe (e.g., imaging probe 4, as shown above in FIG. 1), according to an illustrative embodiment of the invention. The resolution target 1210 is a USAF 6251 resolution target.

Figure 12A:
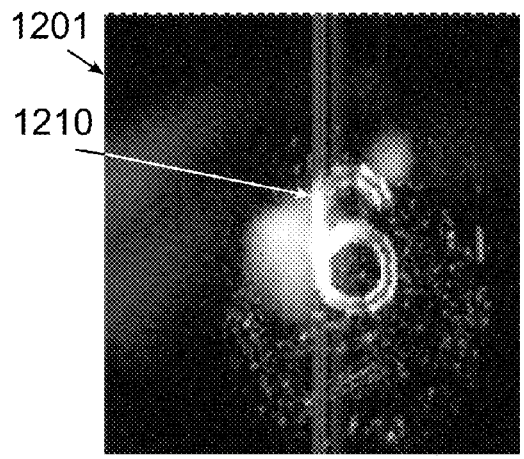
FIGS. 12A-12E show exemplary RCM and PS-OCT images of a resolution target and human skin taken with an apparatus having an imaging probe, according to an illustrative embodiment of the invention.

FIG. 12A shows an en face PS-OCT image 1201 of the resolution target 1210. The PS-OCT image 1201 is obtained through 3-D rendering performed on raster scan data. Multiple adjacent OCT frames are collected and used to generate a 3D data cube.

Figure 12B:
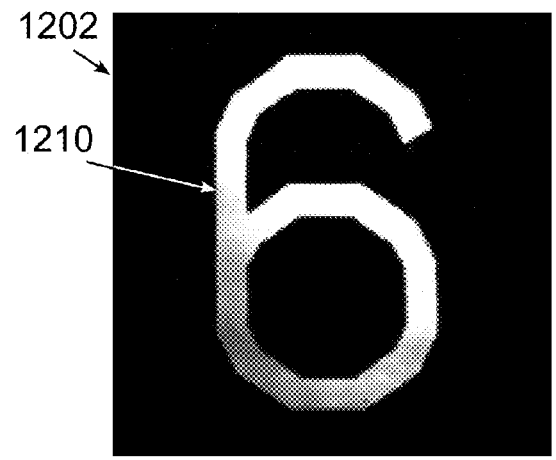

FIG. 12B shows an en face RCM image 1202 of the resolution target 1210. The RCM image 1202 has a better than 1 micron lateral and axial resolution a field of view of about 420×420 μm and an imaging depth of about 300 μm.

Figure 12C:
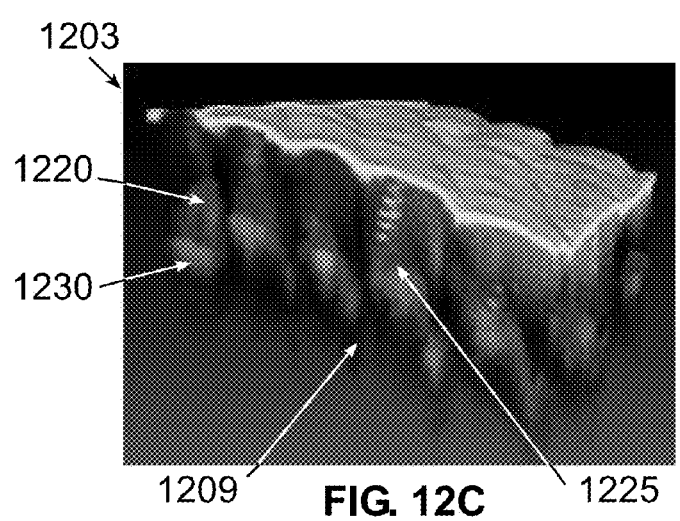

FIG. 12C shows a three dimensional (3-D) PS-OCT image 1203 of human skin 1209 in the palm area. The 3-D PS-OCT image shows an epidermal layer 1220, an underlying dermal layer 1230, and a dermo-epidermal junction 1225. The dermo-epidermal junction 1225 shows "hills and valleys" topography. The PS-OCT image 1203 has an imaging depth of over 1.2 mm and a field of view of about 2×2 mm.

Figure 12D:
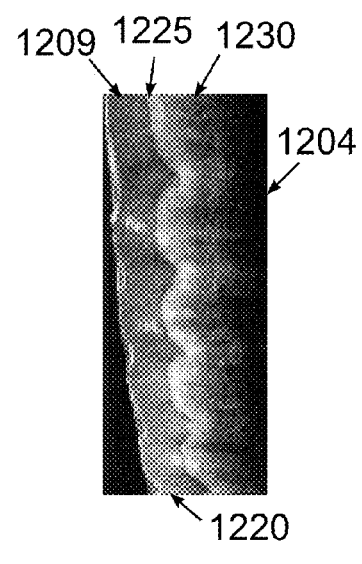

FIG. 12D shows a cross-sectional two dimensional PS-OCT image 1204 of the human skin 1209. The PS-OCT image 1204 shows the epidermal layer 1220, the underlying dermis layer 1230, and the dermo-epidermal junction 1225. The PS-OCT image 1204 has an axial resolution of about 6.8 μm. The axial resolution of the PS-OCT system can be determined by measuring the coherence function with a partial reflector in the sample aim of the interferometer (e.g. sample arm 90B as shown above in FIG. 3). For PS-OCT image 1204, the coherence function has a full width at a half maximum of a coherence peak of 6.8 μm in air. The PS-OCT image 1204 has a sensitivity decay of about 5 dB loss of the sensitivity over a 3.5 mm range.

Figure 12E:
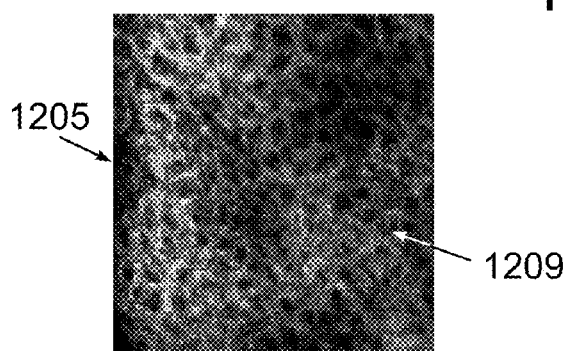

FIG. 12E shows an en face RCM image 1205 of the human skin 1209 at a depth of about 80 μm. The lateral resolution of the RCM channel mode was measured using a high resolution target, USAF 1951-1X. Better than 1 μm lateral resolution was obtained. The 2nd element of the group 9, which has a line width of 0.87 μm, was fully resolved. The sensitivity of a RCM imaging apparatus (e.g., RCM imaging apparatus 8, as described above in FIG. 2) and a PS-OCT unit (e.g., OCT imaging apparatus 12, as described above in FIG. 3) used to generate RCM and OCT images can be measured using a mirror in the sample arm and attenuating the signal with neutral density filters to avoid detector saturation. The PS-OCT unit has a sensitivity of about 112 dB and the RCM unit has a sensitivity of about 60 dB.

FIGS. 13A-13F show exemplary RCM and PS-OCT images of a finger 1301 having a scar area 1310 caused by a minor burn taken with an apparatus having an imaging probe (e.g., imaging probe 4, as shown above in FIG. 1), according to an illustrative embodiment of the invention.

Figure 13A:
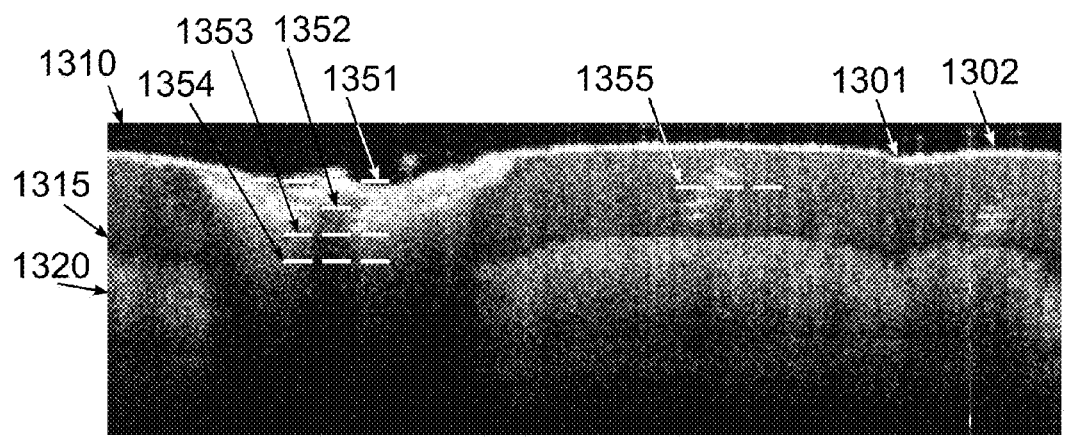
FIGS. 13A-13F show exemplary RCM and PS-OCT images of a finger having a scar area caused by a minor burn taken with an apparatus having an imaging probe, according to an illustrative embodiment of the invention.

More specifically, FIG. 13A shows a cross-sectional PS-OCT image 1302 of the finger 1301. The cross-sectional PS-OCT image 1302 shows an epidermal layer 1315 and dermal layer 1320. The cross-sectional PS-OCT image 1302 shows that that almost the full thickness of the epidermal layer 1315 has been affected in the scar area 1310. The cross-sectional PS-OCT image 1302 shows that the morphology of the dermal layer 1320 cannot be visualized in the scar area 1310, as the deep scar tissue scatters light intensely, but can be visualized outside the scar area 1310. The cross-sectional PS-OCT image 1302 shows depth levels of the finger 1301, specifically, depth levels 1351, 1352, 1353, 1354, and 1355. The cross-sectional PS-OCT image 1302 shows that almost the entire thickness of the epidermal layer 1315 was affected.

In general, FIGS. 13C-13F, 13B show RCM images 1304, 1305, 1306, 1307, 1303, respectively. The RCM images 1304, 1305, 1306, 1307, 1303 are shown at depth levels 1351, 1352, 1353, 1354, 1355, respectively. The RCM images 1304, 1305, 1306, 1307, 1303 are each orthogonal to the PS-OCT image 1302.

Figure 13B:
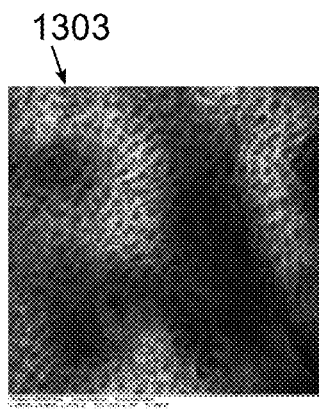
Figure 13C:
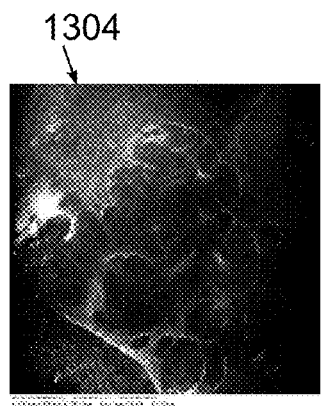
Figure 13D:
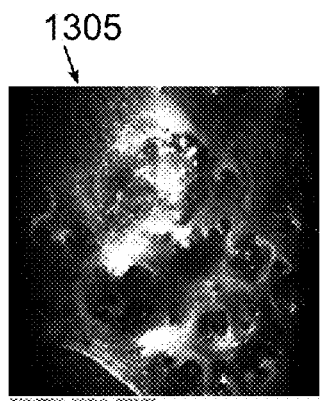
Figure 13E:
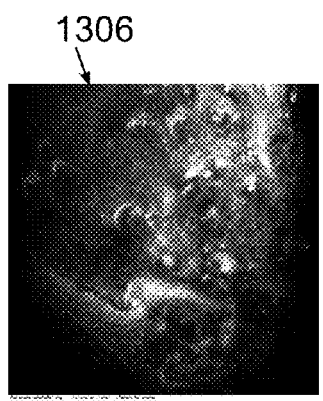
Figure 13F:
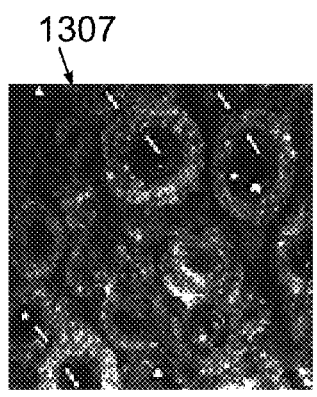

FIG. 13B shows a RCM image 1303 of a normal area of the finger 1301 at a depth of 50 μm. RCM image 1303 shows well differentiated polygonal cells. FIGS. 13C-13F show images of scar tissue without well-differentiated polygonal cells, indicating that the epithelial layer is completely destroyed. FIG. 13C shows a RCM image 1304 of the scar area 1310 at a depth of 10 μm. FIG. 13D shows a RCM image 1305 of the finger 1301 at a depth of 15 μm. FIG. 13E shows a RCM image 1306 of the finger 1301 at a depth of 100 μm. FIG. 13F shows a RCM image 1307 of the finger 1301 at a depth of 150 μm.

FIGS. 14A-14E show cross-sectional PS-OCT and en face RCM images of EpiDermFT™ skin tissue constructs without a burn injury, taken with an apparatus having an imaging probe (e.g. imaging probe 4 as shown above in FIG. 1), according to an illustrative embodiment of the invention. The EpiDermFT™ Skin Model, developed by MatTech, simulates human tissue with high fidelity. EpiDermFT™ is a normal (e.g., non-transformed), human cell-derived, metabolically active, three-dimensional organotypic in vitro skin model. EpiDermFT™ mimics human skin, both structurally and biochemically in a reproducible manner.

Measurements on EpiDermFT™ skin tissue constructs are performed to test the invention's dual-imaging approach. The specimens are kept metabolically active in a small bioreactor. Measurements are performed at room temperature. A specimen is inserted for 1 to 5 seconds into hot water vapors (75° C.).

Figure 14A:
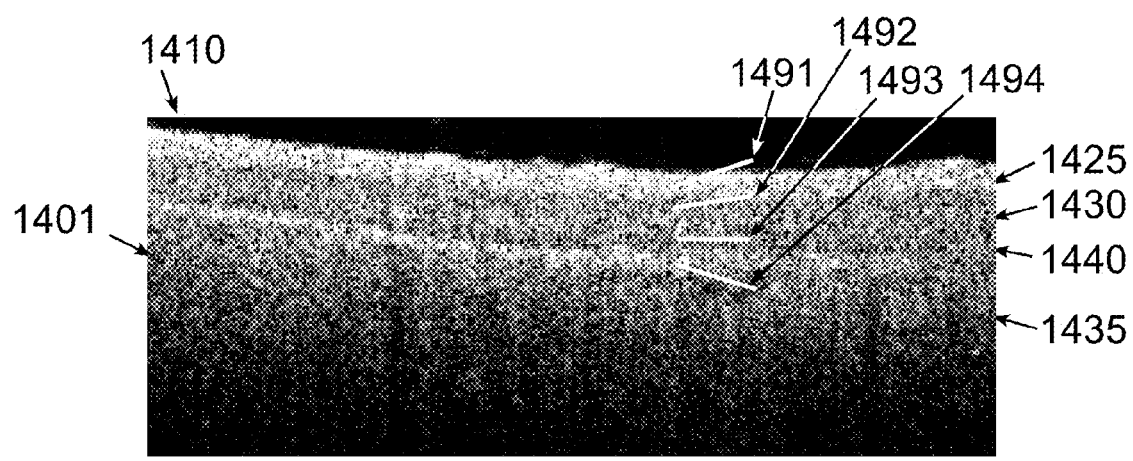
FIGS. 14A-14E show cross-sectional PS-OCT and en face RCM images of EpiDermFT™ skin tissue constructs without a burn injury, taken with an apparatus having an imaging probe, according to an illustrative embodiment of the invention.

FIG. 14A shows a cross-sectional PS-OCT image 1401 of an EpiDermFT™ skin construct 1410 before burn injury. The cross-sectional PS-OCT image 1401 shows exemplary differentiation among a stratum corneum layer 1425, an epidermal layer 1430, and a dermal layer 1435. A DEJ 1440 is visualized. The thickness of the epidermal layer 1430, as shown, is smaller than that of the human skin, while the stratum corneum layer 1425, as shown, is thicker than that of human skin. The cross-sectional PS-OCT image has depth indicators 1491, 1492, 1493, 1494 corresponding to depths of 10 μm, 100 μm, 185 μm and 230 μm, respectively. The RCM images shown in FIGS. 14B, 14C, 14D, 14E, correspond to the depth indicators 1491, 1492, 1493, 1494, respectively.

FIGS. 14B-14E show RCM images showing the tissue morphology of an EpiDermFT™ skin construct (e.g. the EpiDermFT™ skin construct 1410 as shown above in FIG. 14A) at various depths.

Figure 14B:
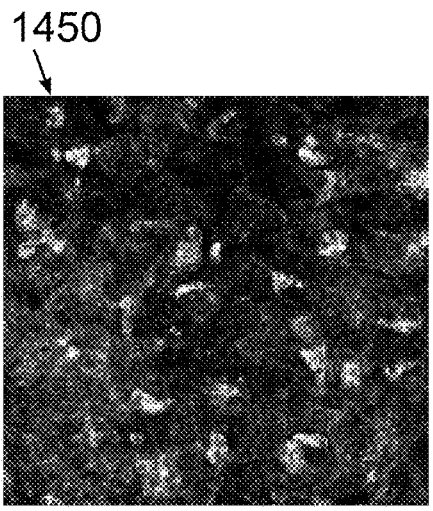
Figure 14C:
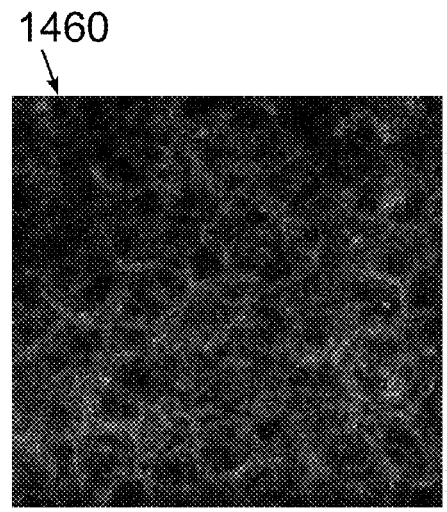
Figure 14D:
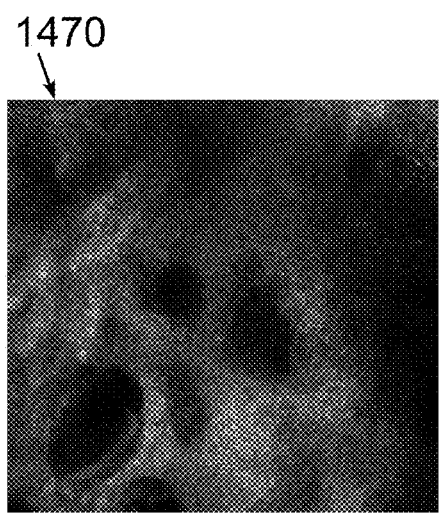
Figure 14E:
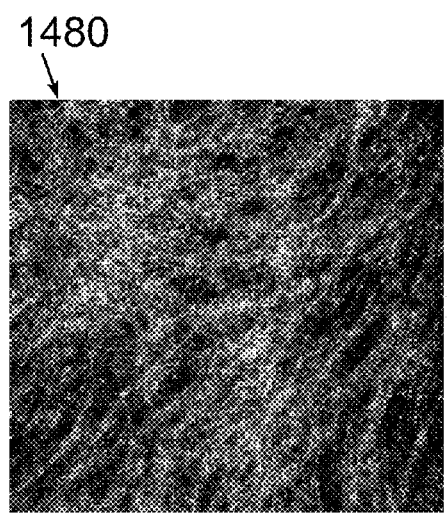

FIG. 14B shows a RCM image 1450 of the EpiDermFT™ skin construct at a depth of 10 μm. The RCM image 1450 shows the tissue morphology of the EpiDermFT™ skin construct in the corneus layer 1425. The corneus layer 1425 has a cobblestone appearance. FIG. 14C shows a RCM image 1460 of the EpiDermFT™ skin construct at a depth of 100 μm. The RCM image 1460 shows polygonal cells in the epidermal layer (e.g. epidermal layer 1430 as shown above in FIG. 14A) similar to the polygonal cell structure found in human skin. FIG. 14D shows a RCM image 1470 of the EpiDermFT™ skin construct at a depth of 185 μm. The RCM image 1470 shows dermal papillae at the dermo-epidermal junction (e.g. dermo-epidermal junction 1440 as shown above in FIG. 14A). FIG. 14E shows a RCM image 1480 of the EpiDermFT™ skin construct 1410 at a depth of 230 μm. The RCM image 1480 shows collagen fibers (e.g., 1485A, 1485B, collectively 1485) in the upper dermal layer (e.g. dermal layer 1435 as shown above in FIG. 14A). As shown, the collagen fibers 1435 are not well aligned, displaying birefringence that is only moderate.

FIGS. 15A-15E show cross-sectional PS-OCT and en face RCM images of EpiDermFT™ skin tissue constructs with a burn injury, taken with an imaging probe (e.g. imaging probe 4 as shown above in FIG. 1), according to an illustrative embodiment of the invention. The images show notable changes in tissue morphology after exposing the specimen in hot water vapors (75° C.).

Figure 15A:
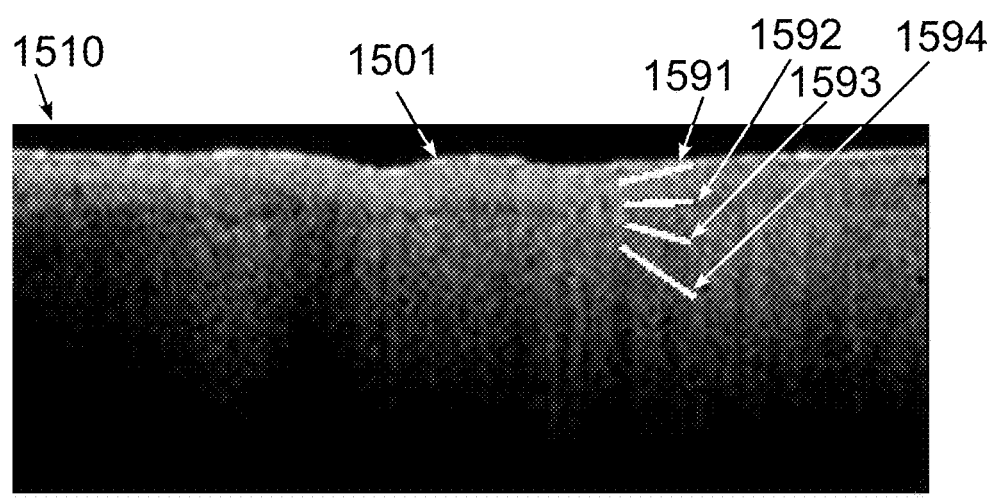
FIGS. 15A-15E show cross-sectional PS-OCT and en face RCM images of EpiDermFT™ skin tissue constructs with a burn injury, taken with an apparatus having an imaging probe, according to an illustrative embodiment of the invention.

FIG. 15A shows a cross-sectional PS-OCT image 1501 of a burn injured EpiDermFT™ skin tissue construct 1510. The cross-sectional PS-OCT image 1501 does not show a well-differentiated dermal-epidermal junction region. The cross-sectional PS-OCT image 1501 shows negligible changes in phase retardance, indicating some degree of destruction in the collagen structure. The cross-sectional PS-OCT image 1501 has depth indicators 1591, 1592, 1593, 1594 corresponding to depths of 10 μm, 100 μm, 150 μm and 220 μm, respectively. The RCM images shown in FIGS. 15B, 15C, 15D, 15E, correspond to the depth indicators 1591, 1592, 1593, 1594, respectively.

Figure 15B:
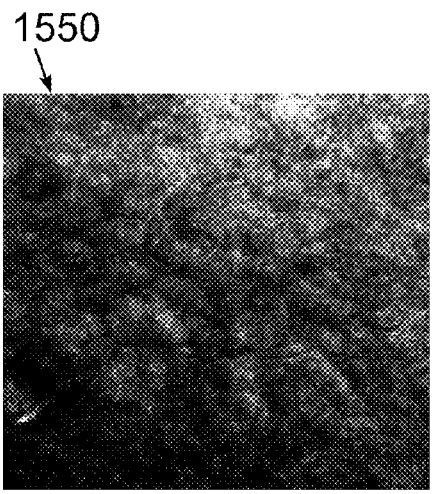
Figure 15C:
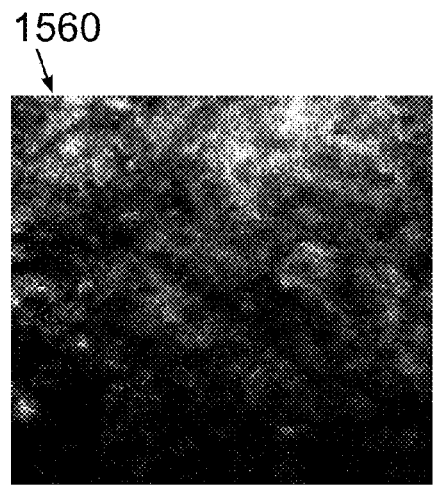
Figure 15D:
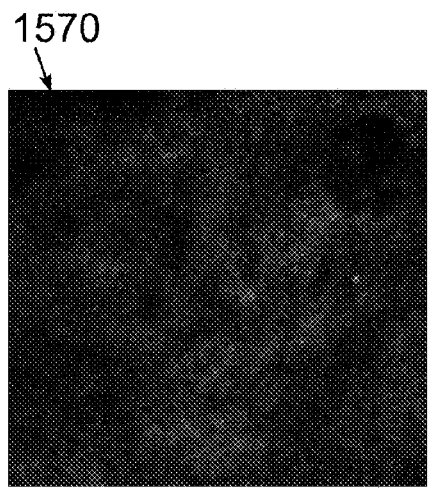
Figure 15E:
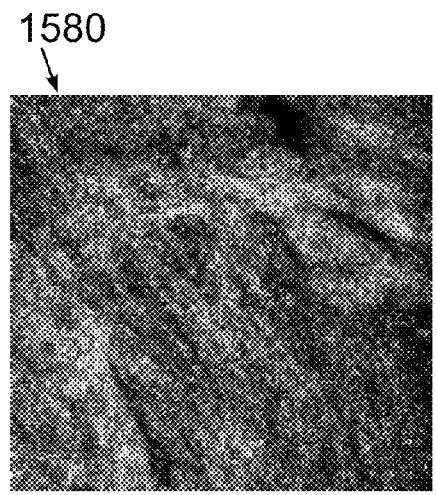

FIGS. 15B-15E show tissue morphology at different depths. FIG. 15B shows a RCM image 1550 of a burn injured EpiDermFT™ skin construct (e.g. the burn injured skin EpiDermFT™ construct 1510 as shown above in FIG. 15A). The RCM image 1550 shows the tissue morphology of the burn injured EpiDermFT™ skin construct at a depth of 10 μm. A cobblestone appearance can no longer be seen. FIG. 15C shows a RCM image 1560 of the burn injured EpiDermFT™ skin construct at a depth of 100 μm. The RCM image 1560 shows that polygonal cells do not exist at the same depth as FIG. 14C. FIG. 15D shows a RCM image 1570 of the burn injured EpiDermFT™ skin construct at a depth of 150 μm. The RCM image 1570 shows that dermal papillae are no longer apparent as in FIG. 14D. FIG. 14E shows a RCM image 1580 of the burn injured EpiDermFT™ skin construct at a depth of 220 μm. The RCM image 1580 shows that collagen fibers are no longer apparent as in FIG. 14E.

Figure 16A:
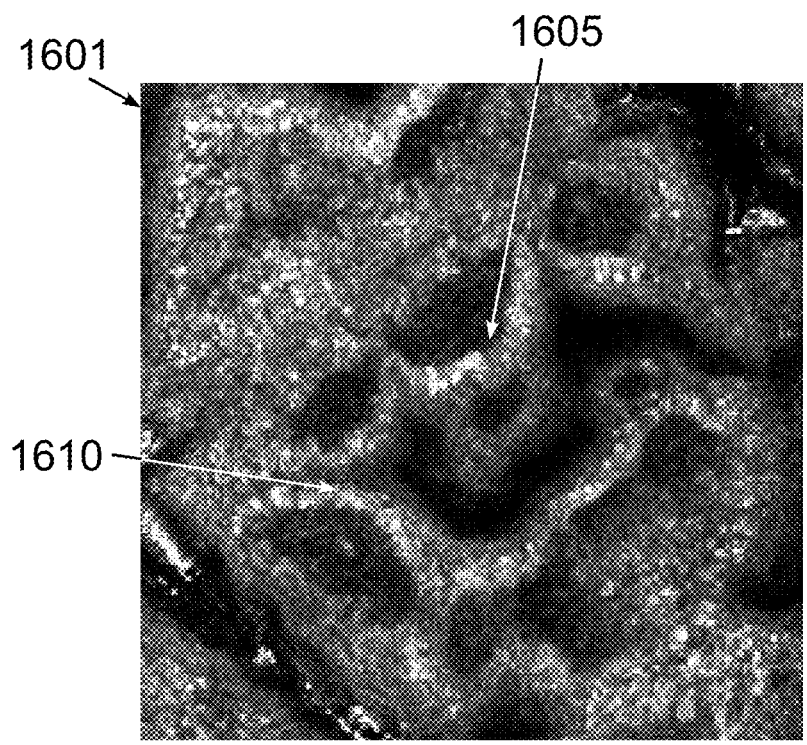
FIGS. 16A-16B show en face RCM images of the upper dermis of human skin taken with an imaging probe, according to an illustrative embodiment of the invention.
Figure 16B:
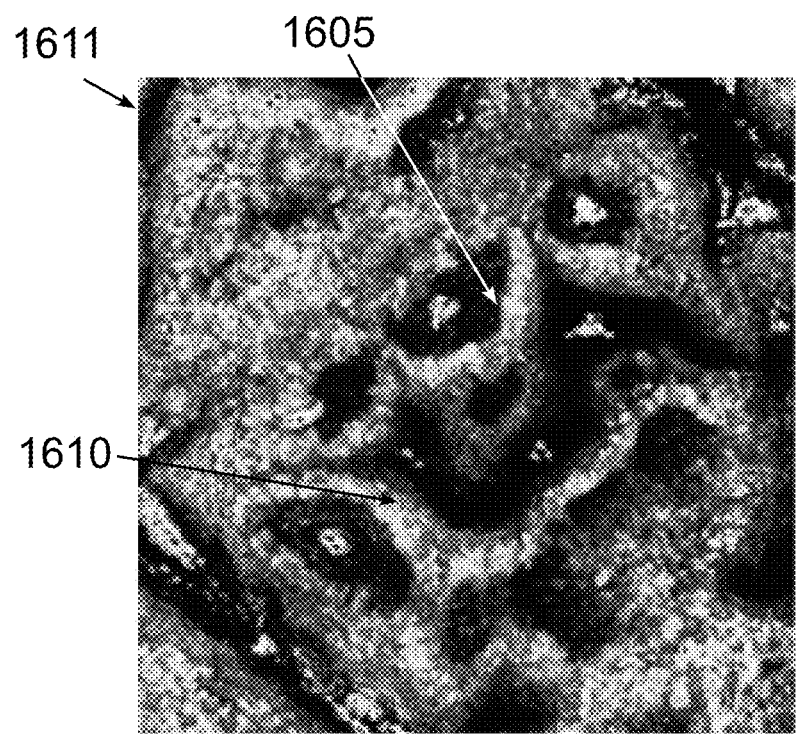

FIGS. 16A-16B show en face RCM images of the upper dermis of human skin taken with an imaging probe (e.g. imaging probe 4 as shown above in FIG. 1), according to an illustrative embodiment of the invention.

FIG. 16A shows a RCM image 1601 of the upper dermis in a volunteer forearm. The RCM image 1601 shows capillaries 1605, 1610. Capillary blood vessels can be present in dermo-epidermal junction region. RCM imaging at video rates can visualize blood flow at a specific depth in real time. Visualizing capillary blood flow can aid in determining tissue viability.

FIG. 16B shows a RCM image 1611 of the same skin region shown above in FIG. 16A after computer processing that emphasizes the presence of capillary blood flow. The RCM image 1611 shows capillaries 1605, 1610. Several frames from RCM movies are used to calculate the standard deviation (SD) of each pixel and depict the capillary blood in the RCM image 1611. The SD of pixel movement is different than zero in the areas where capillary blood flow is present. Attributing different colors to various pixels as a function of the SD value, which correlates to blood flow, can show blood flow in the small capillaries. Taking such maps at different depths and projecting them in two dimensions can show a more complete picture of skin perfusion.

While the invention has been particularly shown and described with reference to specific illustrative embodiments, it should be understood that various changes in form and detail may be made without departing from the spirit and scope of the invention.

What is claimed:

1. A dual-modality imaging apparatus comprising:
  a reflectance confocal microscopy (RCM) imaging apparatus comprising a RCM source;
  an optical coherence tomography (OCT) imaging apparatus comprising an OCT source;
  a dichroic mirror configured to
    (1) reflect, using a first surface, a first beam of light provided by the RCM source toward a sample;
    (2) pass a second beam of light provided by the OCT source through a second surface toward a sample, such that the first beam of light and second beam of light share at least a portion of an imaging path;
    (3) reflect, using the first surface, a first light returning from the sample and direct the first light returning from the sample to the RCM imaging apparatus for imaging; and
    (4) pass, through the first surface, a second light returning from the sample to the OCT imaging apparatus for imaging; and
  an imaging objective having a numerical aperture that is (a) underutilized in the OCT mode to permit imaging depths of greater than one millimeter, and (b) fully utilized in the RCM mode to permit high-resolution imaging, the dual-modality imaging apparatus thereby able to co-register the RCM and OCT images to permit simultaneous acquisition and display of RCM and OCT images,
  wherein underutilizing the numerical aperture in the OCT mode means utilizing between 6.7% and 10.7% of the numerical aperture in the OCT mode.

2. The apparatus of claim 1, further comprising a mirror that reflects the first beam of light toward a dichroic mirror component and reflects the first returning light toward the RCM imaging apparatus.

3. The apparatus of claim 1 wherein the imaging objective has a numerical aperture of 0.8 to 1.0.

4. The apparatus of claim 1 wherein the imaging objective further comprises a broadband coating configured to pass light in the range of 800 nm and 1400 nm.

5. The apparatus of claim 1 wherein the first beam of light fully utilizes the numerical aperture of the imaging objective.

6. The apparatus of claim 1 wherein the first beam of light has a wavelength of 800 to 1000 nanometers.

7. The apparatus of claim 1 wherein the second beam of light has a wavelength of 1200 to 1400 nanometers.

8. The apparatus of claim 1 wherein the OCT imaging apparatus is a polarization-sensitive optical coherence tomography (PS-OCT) imaging apparatus.

9. A method of imaging a sample of biological tissue, comprising:
  providing a first light signal generated by a reflectance confocal microscopy (RCM) source and a second light signal generated by an optical coherence tomography (OCT) source;

delivering, via a common optical path including an imaging objective having a numerical aperture, the first light signal and the second light signal to the sample, the numerical aperture (a) fully utilized by the RCM source, and (b) underutilized by the OCT source to permit imaging depths of greater than one millimeter;

detecting a third light signal from the sample with a RCM imager and a fourth light signal from the sample with an OCT imager; and generating a RCM image based on the third light signal and an OCT image based on the fourth light signal, the method enabling simultaneous acquisition and display of RCM and OCT images, wherein underutilizing the numerical aperture in the OCT mode means utilizing between 6.7% and 10.7% of the numerical aperture in the OCT mode.

10. The method of claim 9 further comprising displaying the RCM image and the OCT image simultaneously.

11. The method of claim 9 wherein the OCT imager is a polarization sensitive OCT (PS-OCT) imager.

12. A method of imaging a sample of biological tissue, comprising:

combining an optical path of a reflectance confocal microscopy (RCM) imager and an optical path of a polarization sensitive optical coherence tomography (OCT) imager using a dichroic mirror and an imaging objective having a numerical aperture of 0.8 to 1.0, wherein the numerical aperture is (a) underutilized by a light beam provided the OCT imager to permit imaging depths of greater than one millimeter, and (b) fully utilized by a light beam provided by the RCM imager;

detecting a first light signal from the sample with the RCM imager and a second light signal from the sample with the OCT imager; and generating a RCM image of the sample using the first light signal and an OCT image of the sample using the second light signal, the RCM and OCT images spatially co-registered and displayed simultaneously, wherein underutilizing the numerical aperture in the OCT mode means utilizing between 6.7% and 10.7% of the numerical aperture in the OCT mode.

13. The method of claim 12 wherein the image acquired from the RCM imager is an image showing nuclear, cellular or sub-cellular details of the sample.

14. The method of claim 12 wherein the image acquired from the OCT imager shows dermal and epidermal layers of human skin in the reflectance mode and a dermal-epidermal junction region in the polarization sensitive mode.

15. The method of claim 12, further comprising diagnosing at least one skin or oral tissue condition.

16. A method of imaging a sample of biological tissue, comprising:

delivering to the sample, via a common optical path including an imaging objective having a numerical aperture of 0.8 to 1.0, a reflectance confocal microscopy (RCM) light beam and a polarization sensitive optical coherence tomography (OCT) light beam, the numerical aperture (a) underutilized by the OCT light beam to permit imaging depths of greater than one millimeter, and (b) fully utilized by the RCM light beam, wherein underutilizing the numerical aperture in the OCT mode means utilizing between 6.7% and 10.7% of the numerical aperture in the OCT mode;

receiving, using a RCM detector, a first light signal from the sample, the detector providing an electrical signal responsive to the first light signal at each of a plurality of locations along the detector, the electrical signal indicative of a RCM image of the sample;

receiving, using an OCT interferometer, a second light signal from the sample, the OCT interferometer combining the second light signal returning from the sample with a reference signal and producing an interference signal indicative of an OCT image of the sample;

generating a RCM image of the sample based on the first electrical signal; and generating an OCT image of the sample based on the interference signal, the RCM and OCT images co-registered or displayed simultaneously.

17. The method of claim 16, further comprising displaying the RCM and OCT images.

18. The method of claim 16 wherein the OCT image is based on two orthogonal polarization states of the interference signal.

19. The method of claim 9 further comprising diagnosing a skin cancer using the RCM and OCT images.

20. The method of claim 19 wherein diagnosing a skin cancer is based on morphological details shown by the RCM image at a location in a dermal-epidermal junction shown by the OCT image.

21. The method of claim 12 further comprising diagnosing a cancerous condition of skin using the RCM and OCT images.

22. The method of claim 21 wherein diagnosing a cancerous condition of skin is based on cellular details of tissue morphology at or near a dermal-epidermal junction region of skin.

23. The method of claim 16 further comprising diagnosing skin cancer using the RCM and OCT images.

24. The method of claim 23 wherein diagnosing skin cancer is based on nuclear or cellular details shown by the RCM image at or near a dermal-epidermal junction region of skin shown by the OCT image.

25. The method of claim 16 wherein the RCM image has a lateral resolution of at least 1 micron.

26. The method of claim 16 wherein an OCT imaging depth is at least 1 mm.

* * * * *